(12) United States Patent
Rasmussen

(10) Patent No.: US 6,524,816 B1
(45) Date of Patent: Feb. 25, 2003

(54) EXPRESSION ELEMENT

(75) Inventor: Preben Rasmussen, Kirke Hyllinge (DK)

(73) Assignee: Danisco A/S, Copenhagen (DK)

( * ) Notice: Subject to any disclaimer, the term of this patent is extended or adjusted under 35 U.S.C. 154(b) by 0 days.

(21) Appl. No.: 09/367,891

(22) PCT Filed: Mar. 2, 1998

(86) PCT No.: PCT/IB98/00312

§ 371 (c)(1),
(2), (4) Date: Dec. 3, 1999

(87) PCT Pub. No.: WO98/38321

PCT Pub. Date: Sep. 3, 1998

(30) Foreign Application Priority Data

Feb. 28, 1997 (GB) .............................................. 9704157

(51) Int. Cl.$^7$ ............................ C12P 21/00; C12N 1/15; C12N 5/00; C07H 21/04
(52) U.S. Cl. ................... 435/69.1; 435/254.1; 435/410; 536/24.1
(58) Field of Search ............................ 435/69.1, 254.1, 435/410; 536/24.1

(56) References Cited

U.S. PATENT DOCUMENTS

| | | | |
|---|---|---|---|
| 5,198,345 A | | 3/1993 | Gwynna et al. |
| 5,610,046 A | * | 3/1997 | Van Ooyen et al. ........ 435/200 |
| 5,679,543 A | | 10/1997 | Lawlis |
| 6,300,114 B1 | * | 10/2001 | Mantyla et al. ............. 435/200 |

FOREIGN PATENT DOCUMENTS

| | | |
|---|---|---|
| EP | 0 418 695 | 3/1991 |
| EP | 0 463 706 | 1/1992 |
| WO | 89/01969 | 3/1989 |
| WO | 94/14965 | 7/1994 |
| WO | 94/24292 | 10/1994 |
| WO | 95/10616 | 4/1995 |
| WO | 96/01323 | 1/1996 |
| WO | 96/15265 | 5/1996 |
| WO | 96/29415 | 9/1996 |
| WO | 96/29416 | 9/1996 |

OTHER PUBLICATIONS

Zeilinger et al. Different inducibility of expression of th etwo xylanase genes xyn1 and xyn2 in *Trichodermal reesei.* J. Biol. Chem. vol. 271(41):25624–25629, 1996.*

S.J. Gurr et al., "The structure and organization of nuclear genes of filamentous fungi", in Kinghorn. J.R. (ed). Gene Structure in Eukaryotic Microbes, IRL Press, pp. 93–139, 1987.

J D Beggs, "Transformation of yeast by a replicating hybrid plasmid", Nature, vol. 275, Sep.1978, pp. 104–108.

Kryoshi Ito et al., "Biosci. Biotech Biochem., 56(6)", *Cloning and Sequencing of the xynA Gene Encoding Xylanase A of Aspergillus kawachii,* pp. 906–912, (1992).

R.J. Gouka et al., "Appl Microbiol Biotechnol, 46", An expression system based on the promoter region of the *Aspargillus awamori* 1,4–E–endoxylanase A gene, pp. 28–35, (1996).

L.M. de Graaff et al, "Xylans and Xylanases", *Structure and Regulation of an Aspergillus Xylanase Gene,* pp. 235–246, (1992).

L.H. de Graaff et al., "Molecular Microbiology 12(3)". Regulation of the xylanase–encoding xINA gene of *Aspergillus tublgensis,* pp. 479–490, (1994).

D Gems et al., "Gene 03883", An autonomously replicating plasmid transforms *Aspergillus nidulans* at high frequency, pp. 61–67, (1991).

J. Rambosek et al., "CRC Cnt Rev. Biotechnol. vol. 6, Issue 4", *Recombinant DNA Filamentous Fungi: Progress and Prospects,* pp. 357–393, (1987).

R.W. Davies, *Heterologous Gene Expression and Protein Secretion in Aspergillus* Chapter 21, pp. 527–561, (1994).

D J Ballance, "Delta Biotechnology Limited", *Transformation Systems for Filamentous Fungi and an Overview of Fungai Gene Structure,* pp. 1–29, (1991).

G Turner. *Vectors for Genetic Manipulation,* Chapter 24, pp. 641–665, (1994).

M.P Broekhuijsen et al., "Journal of Biotechnology. 31". Secretion of heterologous proteins by *Aspergillus niger,* Production of active human interleukin–6 in a protease–deficient mutant by KEX2–like processing of a glucoamylase –hIL 6 fusion protein, pp. 135–145, (1993).

A.R. Goodey et al., "Yeast Biotechnoloy. 13". Expression and secretion of foreign polypeptides in yeast. pp. 400–429 (1987).

D J King et al., "Molecular and Cell Biology of Yeast, Chapter 4", The production of proteins and peptides from *Saccaromyces cerevisiae,* pp. 107–132, (1989).

A Hinnen et al., "Proc. Natl. Acad. Sci. USA, vol 74, No. 4", Transformation of yeast. pp. 1929–1933, (Apr. 1978).

M Ito et al, "Journal of Bacteriology, vol. 163, No. 1", Transformation of Intact Yeast Cells Treated with Alkali Cations, pp. 163–169. (Jan. 1983).

K Wernars et al., "Mol Gen Genet, 209". Cotransformation of *Asperigillus nidulans*: a tool for replacing fungai genes. pp 71–77. (1987).

F P. Buxton et al, "Gene, 37", Tranformation of *Aspergillus niger* using the argB gene of *Aspergillus nidulans,* pp. 207–215, (1985).

(List continued on next page.)

Primary Examiner—Terry McKelvey
Assistant Examiner—William Sandals
(74) *Attorney, Agent, or Firm*—Foley & Lardner

(57) ABSTRACT

The present invention is concerned with the use of the sequence CGGCAGGGTCTC, or a variant, homologue or fragment thereof, as a control element for activating transcription of a nucleotide sequence or nucleotide sequences from a promoter. The invention accordingly provides nucleic acid constructs in which at least one heterologous copy of the element is operatively liniked upstream or downstream of a promoter which is itself operatively linked to a nucleotide sequence.

15 Claims, 11 Drawing Sheets

OTHER PUBLICATIONS

M.J. Daboussi et al, "Current Genet, 15", Transformation of seven species of filamentous fungi using the nitrate reductase gene of *Aspergillus nidulans*, pp. 453–456, (1989).

P.J. Punt et al., "Methods in Enzymology, vol. 216, Chapter 39", Transformation of Filamentous Fungi Based on Hygromycin B and Phleomycin Resistance Markers, pp. 447–457, (1992).

W V Hartingsvedt et al, "Mol Gen Genet, 206", Development of a homologous transformation system for *Aspergillus niger* based on the pyrG gene, pp. 71–75, (1987).

W. Vishniac et al., "Bacteriol. Rev., 21", *The Thiobacilli*, pp. 195–213, (1957).

* cited by examiner

Figure 11

Alignment of Ppr70 and variants among the *xlnB* elements. The start of the sequences is the SnaBI site (5661) into which the elements are inserted.

Wild Type (SEQ ID NO: 17)  gta CGGCAGGGTCTC acatttagggcct CGGCAGGGTCTCGGCAGGGTCTC ggcaggtac gta pPR70-6 (SEQ ID NO: 18)  gta CGGCAGGGTCTC acatttagggcct CGGCAGGGTCTC pPR70-16 (SEQ ID NO: 19)  gta CGGCAGGGTCTC acatttagggcct CGGCAGGGTCTCGGCAGGGTCTC gta pPR70-3 (SEQ ID NO: 20)  gta CGGCAGGGTCTC acatttagggcct CGGCAGGGTCTCGGCAGGGTCTCGGCAGGGTCTC ggcaggtac CGGCAGGGTCTC gta pPR70-5 (SEQ ID NO: 21)  gta CGGCAGGGTCTC acatttagggcct CGGCAGGGTCTCGGCAGGGTCTCGGCAGGGTCTCGGCAGGGTCTC ggcaggtac CGGCAGGGTCTC CGGCAGGGTCTC gta pPR70-4 (SEQ ID NO: 22)  gta CGGCAGGGTCTC acatttagggcct CGGCAGGGTCTCGGCAGGGTCTCGGCAGGGTCTCGGCAGGGTCTC ggcaggtac CGGCAGGGTCTC (GAGACCCTGCCG)$_2$ gta

SEQUENCE LISTING

```
<160> NUMBER OF SEQ ID NOS: 23

<210> SEQ ID NO 1
<211> LENGTH: 2055
<212> TYPE: DNA
<213> ORGANISM: Aspergillus tubingensis
<220> FEATURE:
<221> NAME/KEY: CDS
<222> LOCATION: (721..998, 1063..1462)

<400> SEQUENCE: 1
aattggagct cgactttacg tacgatgata agtagtgata gtatgatcct caaatttaac      60
gcggcggtgg cactctgcta agtcactaac ggcaggagat acaccctaa gttagcacac     120 gctagcattt tccttcctaa ctagatacag gcagtatatc tccgtctaga ttccagtagg    180
attataatca ttgctaaagt agtatacagt gtcctaaatg gtttcatatg ccatccatga    240
ttggatgaga gtcaaccaat gggtcttacg taatgaacaa taaagcattg agccaggatg    300
cattcaacac agcaatagag tcaggctacg caggcggata tcgatgttga catcagcgaa    360
tctagaccct tgaagctcca ctgcctattg tgaacaggcg ttataatttc aggatgtctg    420
caggacctag aaggcgattt aggctgtttc gggagatcaa ttcggctttc caaatcgccc    480
acggatgctc caccgactag gctaaacccc atcacagcga cgtttcaggt acggcagggt   540
ctcacattta gggcctcggc agggtctcgg cagggtctcg gcaggtaccc ttcttaataa    600
aggctaaata gcttctgcag aatcatgggt atatcaggaa cgtctcctcc gtcgctgcag    660
accttctctt cttactccga gccccattga atcaactcct caagccaagt ctctttcaac    720 atg ctt acc aag aac ctt ctc ctc tgc ttc gcc gca gct aag gct gtt   768
Met Leu Thr Lys Asn Leu Leu Leu Cys Phe Ala Ala Ala Lys Ala Val
  1               5                  10                  15 ctg gcc gtt ccc cac gac tct gtc gtc gag cgt tcg gat gcc ttg cac   816
Leu Ala Val Pro His Asp Ser Val Val Glu Arg Ser Asp Ala Leu His
              20                  25                  30 aag ctc tct gag cgt tcg acc ccg agc tcg acc ggc gag aac aac ggt   864
Lys Leu Ser Glu Arg Ser Thr Pro Ser Ser Thr Gly Glu Asn Asn Gly
          35                  40                  45 tat tac tac tcc ttc tgg acc gac ggc ggt gat gtg acc tac acc       912
Tyr Tyr Tyr Ser Phe Trp Thr Asp Gly Gly Asp Val Thr Tyr Thr
      50                  55                  60 aac ggt aac gct ggc tcg tac tcc gtc gag tgg tcc aac gtt ggc aac   960
Asn Gly Asn Ala Gly Ser Tyr Ser Val Glu Trp Ser Asn Val Gly Asn
```

```
                    65                  70                  75                  80
ttt gtt ggt gga aag ggc tgg aac gct gga agt gcg aa  gtaagttaac                    1008
Phe Val Gly Gly Lys Gly Trp Asn Ala Gly Ser Ala Lys
                    85                  90 ctctctcaac ctgtccctct aggtattcag tgaaaaatgc tcacataact tcag g                    1063 gac atc acc tat agc ggc acc ttc acc cct agc ggc aac ggc tac ctc                  1111
Asp Ile Thr Tyr Ser Gly Thr Phe Thr Pro Ser Gly Asn Gly Tyr Leu
            95                  100                 105 tcc gtc tat ggc tgg acc act gac ccc ctg atc gag tac tac atc gtc                  1159
Ser Val Tyr Gly Trp Thr Thr Asp Pro Leu Ile Glu Tyr Tyr Ile Val
110                 115                 120                 125 gag tcc tac ggc gac tac aac ccc ggc agt gga ggc acc tac aag ggc                  1207
Glu Ser Tyr Gly Asp Tyr Asn Pro Gly Ser Gly Gly Thr Tyr Lys Gly
                130                 135                 140 acc tgc acc tcc gat gga tct gtc tac gat atc tac acg gct acc cgt                  1255
Thr Cys Thr Ser Asp Gly Ser Val Tyr Asp Ile Tyr Thr Ala Thr Arg
            145                 150                 155 acc aac gcc cct tct atc caa gga acc gct acc ttc acc cag tac tgg                  1303
Thr Asn Ala Pro Ser Ile Gln Gly Thr Ala Thr Phe Thr Gln Tyr Trp
            160                 165                 170 gtc cga ttc gac cag aac aag aga gtc gga gga act gtt acc act tcc                  1351
Val Arg Phe Asp Gln Asn Lys Arg Val Gly Gly Thr Val Thr Thr Ser
175                 180                 185 aac cac ttc aac gct tgg gct aag ctg ggc atg aac ctg ggt act cac                  1399
Asn His Phe Asn Ala Trp Ala Lys Leu Gly Met Asn Leu Gly Thr His
190                 195                 200                 205 aac tac cag atc ctg gct acc gag ggc tac cag agc agc gga tct tcc                  1447
Asn Tyr Gln Ile Leu Ala Thr Glu Gly Tyr Gln Ser Ser Gly Ser Ser
                210                 215                 220 tcc atc act att cag tgagcttgga tgtccaaccg tgcttgcaga gattgcctgg                  1502
Ser Ile Thr Ile Gln
            225 atgtgggtgt gggaaatgag tgcgatggtg cttgcaatat tgagcagtcg tatgatgtgt               1562 gaaacaatta gttgctcgct atcaatgcac ttgtcatttg aagtccatca agcggtctag               1622 cgtcgtattc ttcttatctc gaaaaagtac attacaaagt atgtcggcag atcgaggcgc               1682 gccactatcc gaaagataac cttttttttgg tctagttgta gcagttctga gacattaacg              1742 tcaagtatta tgcgtgcaag ctcccgtcat attgtagcgg tcatttcgga gtagacgaca               1802 ccggttgatc gagccataac tatgtgagct ataatttgaa cagcaggagt ccagacggtc               1862 ccgacctcag tgattccagt aggcatcttc ttttacacga caaaaaagtg tctcaatctc               1922 agacaaccag caatttcacg ttcgggatgt cccaacttat ctcttatgat cctgcaacac               1982 gtctaccaat gaaagccact ttttactatg taagtaaaaa tcgacaagcc cgtcagcgcc               2042 catggacaag ctt                                                                   2055

<210> SEQ ID NO 2
<211> LENGTH: 226
<212> TYPE: PRT
<213> ORGANISM: Aspergillus tubingensis

<400> SEQUENCE: 2

Met Leu Thr Lys Asn Leu Leu Leu Cys Phe Ala Ala Lys Ala Val
  1               5                  10                  15

Leu Ala Val Pro His Asp Ser Val Val Glu Arg Ser Asp Ala Leu His
                20                  25                  30

Lys Leu Ser Glu Arg Ser Thr Pro Ser Ser Thr Gly Glu Asn Asn Gly
```

```
              35                  40                  45
Tyr Tyr Tyr Ser Phe Trp Thr Asp Gly Gly Asp Val Thr Tyr Thr
         50                  55                  60
Asn Gly Asn Ala Gly Ser Tyr Ser Val Glu Trp Ser Asn Val Gly Asn
 65                  70                  75                  80
Phe Val Gly Gly Lys Gly Trp Asn Ala Gly Ser Ala Lys Asp Ile Thr
                 85                  90                  95
Tyr Ser Gly Thr Phe Thr Pro Ser Gly Asn Gly Tyr Leu Ser Val Tyr
            100                 105                 110
Gly Trp Thr Thr Asp Pro Leu Ile Glu Tyr Tyr Ile Val Glu Ser Tyr
            115                 120                 125
Gly Asp Tyr Asn Pro Gly Ser Gly Gly Thr Tyr Lys Gly Thr Cys Thr
        130                 135                 140
Ser Asp Gly Ser Val Tyr Asp Ile Tyr Thr Ala Thr Arg Thr Asn Ala
145                 150                 155                 160
Pro Ser Ile Gln Gly Thr Ala Thr Phe Thr Gln Tyr Trp Val Arg Phe
                165                 170                 175
Asp Gln Asn Lys Arg Val Gly Gly Thr Val Thr Thr Ser Asn His Phe
            180                 185                 190
Asn Ala Trp Ala Lys Leu Gly Met Asn Leu Gly Thr His Asn Tyr Gln
            195                 200                 205
Ile Leu Ala Thr Glu Gly Tyr Gln Ser Ser Gly Ser Ser Ser Ile Thr
        210                 215                 220
Ile Gln
225

<210> SEQ ID NO 3
<211> LENGTH: 907
<212> TYPE: DNA
<213> ORGANISM: Aspergillus tubingensis

<400> SEQUENCE: 3
cactattggc gccccaccca gtggagactt atactacaag gtatcgggcg gctatctgag      60
caatcggatc ttcttaagcc acaggctaat atcaaaacac ttgtggcgtc tagccttgtt     120
tttatttgac cgtcgggaag ccggttctgc acaaccttt ccctcgcgtt ctactttcca     180
attaggtttc atgcgaagga ctcaattgg caccttcctt aataagtagt gatagtatta     240
tcctcaaatt taacgcggcg gtggcactct gctaagtcac taacggcagg agacactccc     300
tcaagttagc acacgctagc attttctttc ttaactaggt agaagcagta cgtctccgtc     360
tagattccag tagaattata atcattgtta agtagtata cagtgtcata atggttttta     420
catgccatcc atgattggat gagagccaac caatgggtct tacgtaatgg acaatgaagc     480
attcgagcca ggatgcattt aacgcagcaa gagtcaggct acacaggtgg atatcgatgt     540
tcacaaccgt aaatctagac ccttgaagct ccactgccta ttcgaacagg cattatgatt     600
tcaggatgtc tgcaggaccc tagaaggcga tttaggctgt ttcggagatc aattcggctt     660
ccaaatcgcc cacggatgct ccaccgacta ggctaaaccc catcacagcg gacgtttcag     720
gtacggcagg gtctcacatt tagggcctcg gcagggtctc ggcaggtacc cttcttaata     780
aaggctaaat agcttctgca gaatcatggg tatatcagga acgtctcctc cgtcgctgca     840
gaccttctct tcttactccc agtcccattg aatcaactcc tcaagccaag tctctttcaa     900
catgatg                                                               907
```

<210> SEQ ID NO 4
<211> LENGTH: 2967
<212> TYPE: DNA
<213> ORGANISM: Unknown Organism
<220> FEATURE:
<223> OTHER INFORMATION: Description of Unknown Organism: Xylanase A gene

<400> SEQUENCE: 4

| | | | | | |
|---|---|---|---|---|---|
| gaattcatcc | cggtcggtgt | ccagtcccag | gcggtgaact | tacagtagca | agctgtaaac | 60 |
| ttacctcagg | tacactgtca | gaagcagata | atctcattat | tgatgagact | ttcacgctct | 120 |
| cctgagccat | aaaaggagta | ccttttttt | gaagaacagc | tccacatctt | agttactgat | 180 |
| acctcatcac | aagtcgccag | gaaatgccag | taacgtctgc | aggcctgtac | tatttaccaa | 240 |
| gaaggccagg | tcactggtgg | atatacaact | ttgttatagg | ttgcgggagt | cagcccctac | 300 |
| tccctgatgg | gttcccactc | cccagtcatt | tcctactgga | tagtaggctc | ctagagttgg | 360 |
| gtaaagattg | ccaagggttt | aggcccaatc | ttgtatatgc | ttggctaggc | aggacctcgg | 420 |
| taaactgatg | gctcctgcat | tttgacctga | gtatttccag | ctataagcga | gatttgcaat | 480 |
| actctgcctt | catcacctac | agaaagaact | cctcggccaa | ctcccggtgg | cctttgagct | 540 |
| ccaaagtacc | ttcgatcaag | cttcgcgatc | ttttggccag | tgtttctcgc | agcgttaact | 600 |
| gagcctaagg | cttgcatcaa | gaaataaaga | aacataaccc | tgcactacat | acgtcttgta | 660 |
| tgagcgatga | actgtgttca | ttcagtagat | cagtgggtac | ataatcatga | acatactttt | 720 |
| agtaagaaaa | ccttctgcag | gacgccggtc | aagaatcccc | acttccccgc | ctcccccaac | 780 |
| tcgcagccct | tttatccgtc | tgccgtccat | ttagccaaat | gtagtccatt | tagccaagtg | 840 |
| cggtccattt | agccaagacc | agtggctaga | ttgatagcta | gcacaggaaa | cgcatgactg | 900 |
| agacacaact | atagaactgt | ctctggaaat | aggctcgagg | ttgttcaagc | gtttaaggtg | 960 |
| atgcggcaaa | atgcatatga | ctgagctgct | tcatcttgca | gggggaaggg | ataaatagtc | 1020 |
| tttttcgcag | aatataaata | cagggagagt | gggctcgcag | caatattgac | cagcacagcg | 1080 |
| ctgctctcca | gttgcataaa | taccatcacc | aggatttagc | ttcttcaatc | atcatgaagg | 1140 |
| tcactgcggc | ttttgcaggt | cttttggtca | cggcattcgc | cgctcctgtg | ccggaacctg | 1200 |
| ttctggtgtc | gcgaagtgct | ggtattaact | acgtgcaaaa | ctacaacggc | aaccttggtg | 1260 |
| atttcaccta | tgacgagagt | gccggaacat | tttccatgta | ctgggaagat | ggagtgagct | 1320 |
| ccgactttgt | cgttggtctg | ggctggacca | ctggttcttc | taagtgagtg | actgcattct | 1380 |
| ttaaccaaag | tctaggatct | aacgtttttt | agcgctatca | cctactctgc | cgaatacagt | 1440 |
| gcttctggct | cctcttccta | cctcgctgtg | tacggctggg | tcaactatcc | tcaggctgaa | 1500 |
| tactacatcg | tcgaggatta | cggtgattac | aacccttgca | gctcggccac | aagccttggt | 1560 |
| accgtgtact | ctgatggaag | cacctaccaa | gtctgcaccg | acactcgaac | aaacgaaccg | 1620 |
| tccatcacgg | gaacaagcac | gttcacgcag | tacttctccg | ttcgggagag | cacgcgcaca | 1680 |
| tctggaacgg | tgactgttgc | caaccatttc | gacttctggg | cgcagcatgg | gttcggcaat | 1740 |
| agcgacttca | attatcaggt | catggcagtg | gaagcatgga | gcggtgctgg | cagcgccagt | 1800 |
| gtcacgatct | cctcttagga | gatagtgcct | tagtagtcgg | aagatgtcaa | cgcgagcttt | 1860 |
| gttctcagct | ggtgtgatga | tcggatccgg | ttctctagcg | gttacattga | ggctgtataa | 1920 |
| gctgttgtgg | ggccgagctg | tcagcgctgc | gttttcaact | tgcacagata | atcaactctc | 1980 |
| gtttactatt | tcttgcgttt | tctcgctgct | tatcctatcc | atagataata | ttttgctcaa | 2040 |
| tacatattat | ctatatacaa | cttttttcagt | cgcagtagtc | actccgagca | aggcattggg | 2100 |

-continued

```
aaatcggggg atgcgggtg ctgcgtagcc tctaacctag gcatttaaa ggatatttaa      2160 tctccggata tcctatacta acagactcct aatgactgcg gaaaatatag agggccagga      2220
tctctacaat tcgacgaagt tcaatgcaat cagaggggga ataactaatg agagtgcaat      2280
gagttagaga aggacaatat ggcagtctta gtgtggactt acataacgat atggagtata      2340
gaaaaaagtg gggaggtccg tctactatat ataatgccca ttacgtgtat ccgatgcttg      2400
cccattgcca ctgagtaggt gactcttcga gtccacttaa catcggtata tgagaaaatc      2460
atgccccctt tgcaggaaac ttagctttc attccttgtt tgaagccata attatcacga      2520
aacccattaa agacttatct tcctgtaact gaaacaaata tttcgggatt ggaatagcct      2580
tttgcccgac atcagtattt ttttgcgacg gtaaatctgg gagtatacga tgtcctttca      2640
cgcatctcaa caaaactctg tcgcatcggg taacctacgg atagtactgt atccagacgc      2700
attttttcta ataacaggtc actgtgcaat ttccgggaaa gtttctatgt ataatactct      2760
ctcgttgcat ctcaaatatt gtggctgatt gagacccaca ctatgtcttg catctattgt      2820
accatccttg cttgaggcca attggcgcac ctgtacccgg ttaatgatat aatgatgaag      2880
ctgcagctgg ttaccaatgg gaatgacata ccatgtacat aaactgccag cgtcacagag      2940
gagctgtcaa tagtactgaa atctaga                                          2967
```

<210> SEQ ID NO 5
<211> LENGTH: 3311
<212> TYPE: DNA
<213> ORGANISM: Unknown Organism
<220> FEATURE:
<223> OTHER INFORMATION: Description of Unknown Organism: amyA gene

<400> SEQUENCE: 5

```
gttcaattgg gcgtgatgag atgccgtcgc gggtggagtt gtctgcccat cacaataaac        60
ctttgtccaa acatttgcct aattgcccat caccaacggc tttaagaatc atgtacctcg       120
ctcatttgag aagatggaag atgccattgc cacggcagtc gatcaatcta ctggctatgg       180
atggtccgaa ttttccgtcg tcgccttttg ctctaatctc ggtatgacct tcaccgagcg       240
aatcgtagaa tatttaaagg gttgatcgag ccactttgtc gccgatgtct gactctgtcg       300
tgtcacaact gaactgatca gacgaggtca tctgagtctc tcgtcgaaaa aagactcgtt       360
ggatgattct cgatttcaac tcgggacaag tcatagaacg agtagtactt cagttggcca       420
caaaagatga agtctctcgc cgcaattgct gctctgctgt cgcccacact ggtccgggca       480
gcgactccgg atgagtggaa agctcagtcg atctatttca tgctgacgga ccggtttgcg       540
cgtaccgaca attcgaccac ggctcccctgt gacaccactg ccgggtatg caactaaccc       600 tgtgtttctc ttcccgggac gtacaagggg tcttctccat gctaaccgtg cacatgcaga       660
aatattgcgg gggaacatgg cgaggtatca tcaacaacgt aagtggcttc tgattttcgc       720
tcaataatct tcgtcgcgtg actttatttc ctagctggat tacatccagg atatgggctt       780
cacagctatc tggataactc cagtgacagc ccagtgggac gacgatgtgg atgcggcaga       840
tgcaacgtcg tatcacggtt attggcagaa agacctgtgc gcaaccctgc tccatggatc       900
gctggctgca aactcgtgct gatcggtgat tttttttttt ttttttttga aacagatact       960
ctctgaattc gaaattcggc actgccgatg acttgaaagc cctggctgat gcccttcacg     1020
cccgtgggat gcttctcatg gtcgacgtcg tggctaatca ctttgtacgg accatctaca     1080
tacctgggaa acgcgaagaa ggaaaaaaaa aaaaggcgc acgctaacat ttcgcgttta      1140
gggctacggc ggttctcata gcgaggtgga ttactcgatc ttcaatcctc tgaacagcca     1200
```

```
ggattacttc acccgttcct gtctcattga ggactacgac aaccaggaag aagtcgaaca    1260
atgctggctg gccgatactc cgacgacatt gcccgacgtg dacaccacca atcctcaggt    1320
tcggacgttt ttcaacgact ggatcaagag cctggtggcg aactactcca gtatgattgt    1380
tcccgcggta acgctttagg gcttgctcta actgaaatcg acagtcgatg gtctgcgcgt    1440
cgacaccgtt aagcacgtgg agaaagattt ctggcccgac ttcaacgaag ctgctgcgtg    1500
taccgtcggc gaggtgttca acggtgaccc agcgtacacc tgcccatacc aggaagtgct    1560
ggatggcgtt ctgaactatc cgatgtgagt gattccgaaa gttccatcga tcaggctttc    1620
tgacgcatga gaacagctac tatcctgcgc ttgatgcatt caagtctgtc ggcggcaatc    1680
tcggcggctt ggctcaggcc atcaccaccg tgcaggagac ctgcaaggat ccaatctgc    1740 tcggcaattt ccttgagaat cacgacattg ctcgctttgc ttcgtatgga cactcttttt    1800
gaagccctca tcgattgggg atgctgacac ggacaacaac aacaggtaca cggatgacct    1860
tgctctcgcc aagaatggtc tcgctttcat catcctctcg gatggtattc cgatcatcta    1920
cacgggccag gagcagcact acgccggtga tcacgatccc acaaatcgtg aggccgtctg    1980
gctgtctggc tacaataccg acgccgagct gtaccagttc atcaagaagg ccaatggcat    2040
ccgcaacttg gctatcagcc agaacccgga attcacctcc tccaaggtga gtacaataac    2100
aaacttttcg aaaattttt caccggagaa aacctaagat tcggctaaca aaacaaaaaa    2160 aaaaagacc aaggtcatct accaagacga ttcgacccct tgccattaacc ggggcggcgt    2220 cgttactgtc ctgagcaatg aaggcgcctc cggggagacc gggactgtct ccattccggg    2280
aactggcttc gaggccggca cggaattgac tgatgtcatc cctgcaaga ccgtgactgc    2340 gggggacagc ggggcggtcg acgtgcccct gtcgggcgga ctgccaagcg tgctctatcc    2400
cagctcccag ctggccaaga gtggtctgtg tgcgtcggcg tgagggattt ctctcatcac    2460
caggcgatgt caggagacaa tttttttctg aactcagggg tttctcagag agctcaaaat    2520
cgggaacttt ttttttgcag gaactccgag tgtacatata ttgagtggag tctctcattc    2580
gtcttttgtg tagcttaggt tgatccatag tgagtgattt ttcacgttgc tccacgtggt    2640
tttcttgaca gttcgggcta tggggtgtta gccttgttgg gcacgaagat ccacactaaa    2700
atctgacact atgaagtcaa ctcaccatcc tgatcggatt tgtgctctca ttccgtcatt    2760
tgtccaatca actctccgta aacccccatc ctaactccct ccccaagtga acctattccc    2820
tttcttgttt cgtaagctcc ccaaggtcca atggccatgt cactttgatg acgcgtagca    2880
cgtcagctgt tccgtaccctt ttctcgcccg atcagcggcg gcggcggcgg cggcggcggc    2940
agcagcagca gcagcagcag cagcagcagc agcagtcaag gggaccaaac caggaaccca    3000
attcggcagg gagacgcgcc gaatccgccg acgttgaacg cggctaggag attcttcgca    3060
ctttgtccct ttcccattgc tcctcgtcat tgtagccttat tcctagtctc gttaaacccg    3120
gaactagcgg ccgaatgatt tggccaccgc ttccatacta tggtacacct gcgctgtact    3180
ccggacgcag aatgtcggcc tttacgcccc aatccctgta cctcggagtt atggttcgaa    3240
gagtgaatcc tcttcgattg cacacttcat gacacagaag ccgcttcgta atcccaatcc    3300
aattgctgca g                                                        3311
```

<210> SEQ ID NO 6
<211> LENGTH: 7432
<212> TYPE: DNA
<213> ORGANISM: Artificial Sequence
<220> FEATURE:

<223> OTHER INFORMATION: Description of Artificial Sequence: Synthetic pPR70 plasmid

<400> SEQUENCE: 6

| | | | | | | |
|---|---|---|---|---|---|---|
| gatccactag | ttctagagcg | gccgccaccg | cggtggagct | ccagcttttg | ttcccttTag | 60 |
| tgagggttaa | ttgcgcgctt | ggcgtaatca | tggtcatagc | tgtttcctgt | gtgaaattgt | 120 |
| tatccgctca | caattccaca | caacatacga | gccgaagca | taaagtgtaa | agcctggggt | 180 |
| gcctaatgag | tgagctaact | cacattaatt | gcgttgcgct | cactgcccgc | tttccagtcg | 240 |
| ggaaacctgt | cgtgccagct | gcattaatga | atcggccaac | gcgcggggag | aggcggtttg | 300 |
| cgtattgggc | gctcttccgc | ttcctcgctc | actgactcgc | tgcgctcggt | cgttcggctg | 360 |
| cggcgagcgg | tatcagctca | ctcaaaggcg | gtaatacggt | tatccacaga | atcagggat | 420 |
| aacgcaggaa | agaacatgtg | agcaaaaggc | cagcaaaagg | ccaggaaccg | taaaaaggcc | 480 |
| gcgttgctgg | cgttttttcca | taggctccgc | cccctgacg | agcatcacaa | aaatcgacgc | 540 |
| tcaagtcaga | ggtggcgaaa | cccgacagga | ctataaagat | accaggcgtt | tccccctgga | 600 |
| agctccctcg | tgcgctctcc | tgttccgacc | ctgccgctta | ccggatacct | gtccgccttt | 660 |
| ctcccttcgg | gaagcgtggc | gctttctcat | agctcacgct | gtaggtatct | cagttcggtg | 720 |
| taggtcgttc | gctccaagct | gggctgtgtg | cacgaacccc | ccgttcagcc | cgaccgctgc | 780 |
| gccttatccg | gtaactatcg | tcttgagtcc | aacccggtaa | gacacgactt | atcgccactg | 840 |
| gcagcagcca | ctggtaacag | gattagcaga | gcgaggtatg | taggcggtgc | tacagagttc | 900 |
| ttgaagtggt | ggcctaacta | cggctacact | agaaggacag | tatttggtat | ctgcgctctg | 960 |
| ctgaagccag | ttaccttcgg | aaaaagagtt | ggtagctctt | gatccggcaa | acaaaccacc | 1020 |
| gctggtagcg | gtggtttttt | tgtttgcaag | cagcagatta | cgcgcagaaa | aaaggatct | 1080 |
| caagaagatc | ctttgatctt | ttctacgggg | tctgacgctc | agtggaacga | aaactcacgt | 1140 |
| taagggattt | tggtcatgag | attatcaaaa | aggatcttca | cctagatcct | tttaaattaa | 1200 |
| aaatgaagtt | ttaaatcaat | ctaaagtata | tatgagtaaa | cttggtctga | cagttaccaa | 1260 |
| tgcttaatca | gtgaggcacc | tatctcagcg | atctgtctat | ttcgttcatc | catagttgcc | 1320 |
| tgactccccg | tcgtgtagat | aactacgata | cgggagggct | taccatctgg | ccccagtgct | 1380 |
| gcaatgatac | cgcgagaccc | acgctcaccg | gctccagatt | tatcagcaat | aaaccagcca | 1440 |
| gccggaaggg | ccgagcgcag | aagtggtcct | gcaactttat | ccgcctccat | ccagtctatt | 1500 |
| aattgttgcc | gggaagctag | agtaagtagt | tcgccagtta | atagtttgcg | caacgttgtt | 1560 |
| gccattgcta | caggcatcgt | ggtgtcacgc | tcgtcgtttg | gtatggcttc | attcagctcc | 1620 |
| ggttcccaac | gatcaaggcg | agttacatga | tcccccatgt | tgtgcaaaaa | agcggttagc | 1680 |
| tccttcggtc | ctccgatcgt | tgtcagaagt | aagttggccg | cagtgttatc | actcatggtt | 1740 |
| atggcagcac | tgcataattc | tcttactgtc | atgccatccg | taagatgctt | ttctgtgact | 1800 |
| ggtgagtact | caaccaagtc | attctgagaa | tagtgtatgc | ggcgaccgag | ttgctcttgc | 1860 |
| ccggcgtcaa | tacgggataa | taccgcgcca | catagcagaa | ctttaaaagt | gctcatcatt | 1920 |
| ggaaaacgtt | cttcggggcg | aaaactctca | aggatcttac | cgctgttgag | atccagttcg | 1980 |
| atgtaaccca | ctcgtgcacc | caactgatct | tcagcatctt | ttactttcac | cagcgtttct | 2040 |
| gggtgagcaa | aaacaggaag | gcaaaatgcc | gcaaaaaagg | gaataagggc | gacacggaaa | 2100 |
| tgttgaatac | tcatactctt | ccttttcaa | tattattgaa | gcatttatca | gggttattgt | 2160 |
| ctcatgagcg | gatacatatt | tgaatgtatt | tagaaaaata | aacaaatagg | ggttccgcgc | 2220 |

-continued

| | | | | | |
|---|---|---|---|---|---|
| acatttcccc | gaaaagtgcc | acctaaattg | taagcgttaa | tattttgtta | aaattcgcgt | 2280 |
| taaattttg | ttaaatcagc | tcattttta | accaataggc | cgaaatcggc | aaaatcccctt | 2340 |
| ataaatcaaa | agaatagacc | gagatagggt | tgagtgttgt | tccagtttgg | aacaagagtc | 2400 |
| cactattaaa | gaacgtggac | tccaacgtca | aagggcgaaa | aaccgtctat | cagggcgatg | 2460 |
| gcccactacg | tgaaccatca | ccctaatcaa | gttttttggg | gtcgaggtgc | cgtaaagcac | 2520 |
| taaatcggaa | ccctaaaggg | agcccccgat | ttagagcttg | acggggaaag | ccggcgaacg | 2580 |
| tggcgagaaa | ggaagggaag | aaagcgaaag | gagcgggcgc | tagggcgctg | gcaagtgtag | 2640 |
| cggtcacgct | gcgcgtaacc | accacacccg | ccgcgcttaa | tgcgccgcta | cagggcgcgt | 2700 |
| cccattcgcc | attcaggctg | cgcaactgtt | gggaagggcg | atcggtgcgg | gcctcttcgc | 2760 |
| tattacgcca | gctggcgaaa | gggggatgtg | ctgcaaggcg | attaagttgg | gtaacgccag | 2820 |
| ggttttccca | gtcacgacgt | tgtaaaacga | cggccagtga | gcgcgcgtaa | tacgactcac | 2880 |
| tatagggcga | attggcgggc | ccgtctctca | tccatggttc | ctcttcggcc | tcgaccatcc | 2940 |
| catcactgcc | atacctgcac | tcgttgtttt | ctcttgcatt | cacatcgcgg | tgttcatcca | 3000 |
| cgaacatcat | ctatccgata | aggctgatga | ggagaactat | gtatatccta | tgaccagtgg | 3060 |
| gtcgtcagat | ccctacttca | tacgcaattc | gttgagctat | actcgatgat | cgttgataag | 3120 |
| aatccactga | ctacttatta | cggtgtacaa | cgtgcactat | ttcagcgaca | ggcgtgcctc | 3180 |
| actgcctagt | gcctacaggt | aacactcaac | agaatgcaca | aggatggagc | gtccaaaacg | 3240 |
| gaatgccttg | tgacgtcagt | cagtgcgctg | ccactaatgt | tatactagtac | tcctctctgt | 3300 |
| accaccaccg | cccaccccgga | caagatactc | cgtatagttc | tccgatgcac | cgcatcttgc | 3360 |
| gacccaccca | gacctcaaag | atatgcctcc | aggatgacgg | tatcgctctc | tgagaaaccc | 3420 |
| ctgagttcag | aaaaaattg | tctcctgaca | tcgcctggtg | atgagagaat | ccctcacgc | 3480 |
| cgacgcacac | agaccactct | tggccagctg | ggagctggga | tagagcacgc | ttggcagtcc | 3540 |
| gcccgacaag | ggcacgtcga | ccgccccgct | gtccccgca | gtcacggtct | tgcaggagat | 3600 |
| gacatcagtc | aattccgtgc | cggcctcgaa | gccagttccc | ggaatggaga | cagtcccggt | 3660 |
| ctccccggag | gcgccttcat | tgctcaggac | agtaacgacg | ccgccccggt | taatggcaag | 3720 |
| ggtcgaatcg | tcttggtaga | tgaccttggt | cttttttttt | tttgttttgt | tagccgaatc | 3780 |
| ttaggttttc | tccggtgaaa | aatttttcga | aaagtttgtt | attgtactca | ccttggagga | 3840 |
| ggtgaattcc | gggttctggc | tgatagccaa | gttgcggatg | ccattggcct | tcttgatgaa | 3900 |
| ctggtacagc | tcggcgtcgg | tattgtagcc | agacagccag | acggcctcac | gatttgtggg | 3960 |
| atcgtgatca | ccgcgctagt | gctgctcctg | gcccgtgtag | atgatcggaa | taccatccga | 4020 |
| gaggatgatg | aaagcgagac | cattcttggc | gagagcaagg | tcatccgtgt | acctgttgtt | 4080 |
| gttgtccgtg | tcagcatccc | caatcgatga | gggcttcaaa | aagagtgtcc | atacgaagca | 4140 |
| aagcgagcaa | tgtcgtgatt | ctcaaggaaa | ttgccgagca | gattggaatc | cttgcagctc | 4200 |
| tcctgcacgg | tggtgatggc | ctgagccaag | ccgccgagat | tgccgccgac | agacttgaat | 4260 |
| gcatcaagcg | caggatagta | gctgttctca | tgcgtcagaa | agcctgatcg | atggaacttt | 4320 |
| cggaatcact | cacatcggat | agttcagaac | gccatccagc | acttcctggt | atgggcaggt | 4380 |
| gtacgctggg | tcaccgttga | acacctcgcc | gacggtacac | gcagcagctt | cgttgaagtc | 4440 |
| gggccagaaa | tctttctcca | cgtgcttaac | ggtgtcgacg | cgcagaccat | cgactgtcga | 4500 |
| tttcagttag | agcaagccct | aaagcgttac | cgcgggaaca | atcatactgg | agtagttcgc | 4560 |
| caccaggctc | ttgatccagt | cgttgaaaaa | cgtccgaacc | tgaggattgg | tggtgtccac | 4620 |

```
gtcgggcaat gtcgtcggag tatcggccag ccagcattgt tcgacttctt cctggttgtc    4680
gtagtcctca atgagacaga acgggtggaa gtaatcctgg ctgttcagag gattgaagat    4740
cgagtaatcc acctcgctat gagaaccgcc gtagccctaa acgcgaaatg ttagcgtgcg    4800 ccttttttt tttttccttc ttcgcgtttc ccaggtatgt agatggtccg tacaaagtga    4860
ttagccacga cgtcgaccat gagaagcatc ccacgggcgt gaagggcatc agccagggct    4920
ttcaagtcat cggcagtgcc gaatttcgaa ttcagagagt atctgtttca aaaaaaaaa    4980 aaaaaaatc accgatcagc acgagtttgc agccagcgat ccatggagca gggttgcgca    5040
caggtctttc tgccaataac cgtgatacga cgttgcatct gccgcatcca catcgtcgtc    5100
ccactgggct gtcactggag ttatccagat agctgtgaag cccatatcct ggatgtaatc    5160
cagctaggaa ataaagtcac gcgacgaaga ttattgagcg aaaatcagaa gccacttacg    5220
ttgttgatga tacctcgcca tgttcccccg caatatttct gcatgtgcac ggttagcatg    5280
gagaagaccc cttgtacgtc ccgggaagag aaacacaggg ttagttgcat accccggcag    5340
tggtgtcaca gggagccgtg gtcgaattgt cggtacgcgc aaaccggtcc gtcagcatga    5400
aatagatcga ctgagctttc cactcatccg gagtcgctgc ccggaccagt gtgggcgaca    5460
gcagagcagc aattgcggcg agagacttca tcttttgtgg ccaactgaag taattcctgc    5520
agcccttgaa agagacttgg cttgaggagt tgattcaatg gggctcggag taagaagaga    5580
aggtctgcag cgacggagga gacgttcctg atatacccat gattctgcag aagctattta    5640
gcctttatta agaagggtac gtacctgccg agaccctgcc gagaccctgc cgaggcccta    5700
aatgtgagac cctgccgtac ctgaaacgtc gctgtgatgg ggtttagcct agtcggtgga    5760
gcatccgtgg gcgatttgga aagccgaatt gatctcccga aacagcctaa atcgccttct    5820
aggtcctgca gacatcctga aattataacg cctgttcaca ataggcagtg gagcttcaag    5880
ggtctagatt cgctgatgtc aacatcgggg ggatcgcagg gaaaaatacg agctccaatg    5940
aacctgggtg tggcaacttc aatggaaagg aactgccttt gcaggtgtgg ctgaacccca    6000
cggttccggt cggaggcggc gaaatcaccc gatgtggctg gtcgtggag ggtcgcgatg    6060 atttactgag ctcctctttt gctcgacatt gaatgtgcat tgttcacctc atataagggc    6120
cagtcgctgc taaattattc ggtagtattt gcgcatctct ggatctacca attagggcct    6180
atcagtcgaa actccaagct actcatattg cacaagcctc tttcatcccc gcattaaccc    6240
ctccaccgac accatgtcct ccaagtcgca attgacctac actgcccgtg ccagcaagca    6300
ccccaatgct ctggccaagc ggctgttcga aattgctgag gccaagaaga ccaatgtgac    6360
cgtctctgcc gacgttacca ccactaagga gctactagat cttgctgacc gtaggccgac    6420
ccgccattct gcctgtttat gctgcataca aacttattaa cggtgatacc ggactgaggt    6480
ctcggtccct acatcgccgt gatcaaaacc cacatcgata tcctctctga cttcagcgac    6540
gagaccattg agggcctcaa ggctcttgcg cagaagcaca acttcctcat cttcgaggac    6600
cgcaaattca tcgacattgg caacactgtc cagaagcaat accaccgtgg taccctccgc    6660
atctcagaat gggcccatat catcaactgc agcatcctgc ctggcgaggg tatcgtcgag    6720
gctctcgctc agacgcgtc tgcaccggac ttctcctacg gccccgaacg tggtctgttg    6780
atcttggcgg aaatgacctc taagggttcc ttggccaccg gccagtacac tacttcttcg    6840
gttgattatg cccggaaata caagaacttc gtcatgggat ttgtgtcgac ccgctcgttg    6900
ggtgaggtgc agtcggaagt cagctctcct tcggatgagg aggactttgt ggtcttcacg    6960
```

```
actggtgtga acatttcgtc caagggagat aagctcggtc agcagtacca gactcccgca    7020
tcggctatcg gtcggggtgc tgacttcatt atcgcgggtc gcggtatcta cgccgcgccg    7080
gacccggtgc aggctgcgca acagtaccag aaggaaggtt gggaggcgta cctggcccgt    7140
gtcggcggaa actaatacta taaaatgagg aaaaagtttt tgatggttat gaatgatata    7200
gaaatgcaac ttgccgctac gatacgcata caaactaatg tcgagcacgg gtagtcagac    7260
tgcggcatcg gatgtcaaaa cggtattgat cctgcaggct attatagggt ggcacgggat    7320
taatgcggta cgacgatttg atgcagataa gcaggctgcg aagtacttag tcctgtaact    7380
cttgcgtaga gcaaatggcg acgggtggct gataagggac ggtgataagc tt           7432
```

<210> SEQ ID NO 7
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

```
cggcagggtc tc                                                          12
```

<210> SEQ ID NO 8
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
gagaccctgc cg                                                          12
```

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
tcgactgagc tttccactca t                                                21
```

<210> SEQ ID NO 10
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

```
tacgtacctg ccgagaccct gccgagaccc tgccgaggcc ctaaatgtga gaccctgccg    60
tac                                                                   63
```

<210> SEQ ID NO 11
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 11
tacgagaccc tgccgaggcc ctaaatgtga gaccctgccg tac                43

<210> SEQ ID NO 12
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tacgagaccc tgccgagacc ctgccgaggc cctaaatgtg agaccctgcc gtac      54

<210> SEQ ID NO 13
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tacgagaccc tgccggtacc tgccgagacc ctgccgagac cctgccgagg ccctaaatgt   60
gagaccctgc cgtac                                                    75

<210> SEQ ID NO 14
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tacgagaccc tgccggagac cctgccggta cctgccgaga ccctgccgag accctgccga   60
ggccctaaat gtgagaccct gccgtac                                       87

<210> SEQ ID NO 15
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tacgagaccc tgccgcggca gggtctccgg cagggtctcg tacctgccga gaccctgccg   60
agaccctgcc gaggccctaa atgtgagacc ctgccgtac                          99

<210> SEQ ID NO 16
<211> LENGTH: 22
<212> TYPE: DNA
<213> ORGANISM: Unknown Organism
<220> FEATURE:
<223> OTHER INFORMATION: Description of Unknown Organism: Illustrative
      overlapping element

<400> SEQUENCE: 16
ggcagggtct cggcagggtc tc                                            22

<210> SEQ ID NO 17
<211> LENGTH: 63
<212> TYPE: DNA
```

<210> SEQ ID NO 17
<211> LENGTH: 63
<212> TYPE: DNA
<213> ORGANISM: Artificial Sequence
<220> FEATURE:
<223> OTHER INFORMATION: Description of Artificial Sequence: Synthetic pPR70

<400> SEQUENCE: 17
gtacggcagg gtctcacatt tagggcctcg gcagggtctc ggcagggtct cggcaggtac    60
gta                                                                  63

<210> SEQ ID NO 18
<211> LENGTH: 43
<212> TYPE: DNA
<213> ORGANISM: Artificial Sequence
<220> FEATURE:
<223> OTHER INFORMATION: Description of Artificial Sequence: Synthetic pPR70-6

<400> SEQUENCE: 18
gtacggcagg gtctcacatt tagggcctcg gcagggtctc gta                      43

<210> SEQ ID NO 19
<211> LENGTH: 54
<212> TYPE: DNA
<213> ORGANISM: Artificial Sequence
<220> FEATURE:
<223> OTHER INFORMATION: Description of Artificial Sequence: Synthetic pPR70-16

<400> SEQUENCE: 19
gtacggcagg gtctcacatt tagggcctcg gcagggtctc ggcagggtct cgta          54

<210> SEQ ID NO 20
<211> LENGTH: 75
<212> TYPE: DNA
<213> ORGANISM: Artificial Sequence
<220> FEATURE:
<223> OTHER INFORMATION: Description of Artificial Sequence: Synthetic pPR70-3

<400> SEQUENCE: 20
gtacggcagg gtctcacatt tagggcctcg gcagggtctc ggcagggtct cggcaggtac    60
cggcagggtc tcgta                                                     75

<210> SEQ ID NO 21
<211> LENGTH: 87
<212> TYPE: DNA
<213> ORGANISM: Artificial Sequence
<220> FEATURE:
<223> OTHER INFORMATION: Description of Artificial Sequence: Synthetic pPR70-5

<400> SEQUENCE: 21
gtacggcagg gtctcacatt tagggcctcg gcagggtctc ggcagggtct cggcaggtac    60
cggcagggtc tccggcaggg tctcgta                                        87

<210> SEQ ID NO 22
<211> LENGTH: 96
<212> TYPE: DNA
<213> ORGANISM: Artificial Sequence
<220> FEATURE:
<223> OTHER INFORMATION: Description of Artificial Sequence: Synthetic pPR70-4

<400> SEQUENCE: 22
gtacggcagg gtctcacatt tagggcctcg gcagggtctc ggcagggtct cggcaggtac    60

```
cggcagggtc tcgagaccct gccggagacc ctgccg                                    96

<210> SEQ ID NO 23
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gtccatttag cca                                                             13
```

EXPRESSION ELEMENT

This application is a 371 submission of PCT/IB98/00312 filed Mar. 2, 1998 which claims priority to GB 9704157.8 filed Feb. 28, 1997.

The present invention relates to an expression element suitable for increasing the levels of expression of polypeptides in cells or organisms. In particular, the invention relates to an expression element having the sequence (SEQ ID NO: 7) CGGCAGGGTCTC.

Xylan, a heterogeneous polysaccharide commonly found in plant cell walls, is one of the most common polysaccharides in nature. Xylanase is one of the major enzymes involved in the breakdown of xylan, catalysing the digestion of xylan into oligoxylose subunits.

Xylanase enzymes and corresponding genes have been isolated from a very large number of different organisms. Examples include xylanases A and B from Penicillium, xylanase A from *Thermotoga maritima* and *Bacillus subtilis*, xylanases B and D from *Ruminococcus flavefaciens*, and many others.

It is generally established that it is desirable to direct expression of a heterologous nucleotide sequence in an organism, such as a filamentous fungus (e.g. *Aspergillus niger*), or yeast. The resultant protein or enzyme may then be used in industry. Alternatively, the resultant protein or enzyme may be useful for the organism itself. For example, it may be desirable to produce fungal protein products with an optimised amino acid composition and so increase the nutritive value thereof. For example, the fungus may be made more useful as a feed. In the alternative, it may be desirable to isolate the resultant protein or enzyme and then use the protein or enzyme to prepare, for example, food compositions. In this regard, the resultant protein or enzyme can be a component of the food composition or it can be used to prepare food compositions, including altering the characteristics or appearance of food compositions. It may even be desirable to use the organism, such as a filamentous fungus or a yeast, to express heterologous genes, such as for the same purposes.

Filamentous fungi in particular are attractive hosts for the large-scale production of proteins in industry. They have the capacity to secrete a large amount of heterologous and/or homologous protein into their growth medium, they have been extensively studied and are well known, and moreover they are considered safe for use in the preparation of products useful in the food, feed and beverage industries. They are known for their ability to secrete several hydrolytic enzymes, amongst which number the xylanases. A number of different xylanases are known and have been characterised and/or cloned (for example, see Ito, et al., (1992) Biosci. Biotech. Biochem. 56:906–912), including xylanases from *A. awamori, A. kawachii* and xylanases A, B and C from *Aspergillus tubingensis*. Of the latter, xylanase B is known to be more weakly expressed (see WO 94/14965). In general, xylanases belong to one of two families of glycosyl hydrolases, family H and family F. There is little homology between the two families, but within each family there is some sequence identity. For example, xylanases A and B of *A. tubingensis* belong to family H and share approximately 45% sequence identity at the amino acid level.

For heterologous expression in filamentous fungi, as well as the vast majority of other organisms, it is desirable to use a strong promoter to direct expression of the gene in question. Usually it is assumed that highly expressed genes contain a strong promoter and consequently promoters derived from highly expressed genes are frequently used for this purpose. Examples of expression systems for use in filamentous fungi include systems employing the glucoamylase promoter (U.S. Pat. No. 5,198,345) and the *A. awamori* xylanase A (xlnA) promoter (Gouka, et al., (1996) Appl. Microbiol. Biotechnol. 46, 28–35).

De Graaff et al., in xylans and xylanases, J. Visser et al. (eds.), 1992:235–246, Elsevier, and De Graaff et al., (1994) Molecular Microbiology 12:479–490, have identified a 158 bp upstream regulatory region of the *A. tubingensis* xlnA gene which is responsible for activation of transcription from the xlnA promoter. This region contains inter alia a sequence which comprises three repeats of the element (SEQ ID NO: 23) GTCCATTTAGCCA. De Graaff et al. showed that the entire 158 bp region was capable of activating an *A. niger* glucose oxidase gene (goxC) core promoter. It was not, however, determined whether the element (SEQ ID NO: 23) GTCCATTTAGCCA was itself responsible for the activity of the upstream region or the activating effect.

According to a first aspect of the present invention there is provided the use of a nucleic acid element having the sequence (SEQ ID NO: 7) CGGCAGGGTCTC to modulate transcription of a nucleotide sequence from a promoter.

Preferably, the promoter is a core promoter.

The present invention is concerned with the use of the sequence (SEQ ID NO: 7) CGGCAGGGTCTC as a control element for modulating transcription of a nucleotide sequence or nucleotide sequences from a promoter. The invention accordingly provides nucleic acid constructs in which at least one heterologous copy of the element is operatively linked to a promoter which is itself operatively linked to a nucleotide sequence, vectors containing such nucleic acid constructs and host cells transformed with such vectors and/or expressing DNA constructs according to the invention. Moreover, the invention concerns the use of multiple copies of the activating element operatively linked to the promoter, in order to provide further activation of transcription. In a further aspect, the invention concerns a sequence variant of the *A. tubingensis* xlnB gene which possesses enhanced expression characteristics as a result of the presence of three, rather than two, copies of the element of the invention upstream of the TATA box, as well as the use of this variant in nucleic acid constructs as above.

The element according to the invention is preferably placed upstream of a promoter which is operatively linked to a nucleotide sequence. The nucleotide sequence is preferably a heterologous nucleotide sequence.

Where a promoter already contains, in its upstream sequences, one or two copies of the regulatory element of the invention, an exogenous copy or copies is added in accordance with the invention in order to further activate transcription from this promoter.

The optimum number of elements is three. The presence of more than three elements is detrimental to transcriptional activation. The use of four or more elements is applicable where a lower, but still significant, level of transcription is desired. Thus, the invention may be applied to the modulation (downregulation as well as the upregulation) of transcription from a promoter. Preferably, the element of the invention is used to upregulate transcription from the promoter, such that the rate of transcription is increased.

Where more than one copy of the element of the invention is present, the elements may overlap. Thus, for example, the initial nucleotide of one element may also be the terminal nucleotide of another element. Preferably, the elements overlap by 1, 2 or 3 nucleotides. Preferably, the sequence of an overlapping element is (SEQ ID NO: 16) GGCAGGGTCTCGGCAGGGTCTC.

Preferably, the activated promoter linked to the nucleotide sequence according to the invention is incorporated into a nucleic acid construct, which may be a plasmid vector or the like. Advantageously, a vector according to the invention is an expression vector.

As stated above, three copies of the element provide the strongest transcriptional activation, being highly preferred to two elements. The addition of further elements, above three, leads to a progressive reduction in the activation level, as described in further detail in the accompanying examples.

Expression vectors according to the invention are useful for transforming cells. The invention accordingly provides cells transformed with vectors according to the invention, for the expression of polypeptides encoded by the heterologous nucleotide sequence.

The transformed cells may be cultured cells, for example in tissue culture or organ culture, but also cells which form all or part of a discrete living organism. The invention accordingly provides a transgenic non-human organism which has been transformed with a nucleic acid construct according to the invention. Such organisms may be unicellular or multicellular. Especially preferred are yeasts and filamentous fungi, especially Aspergillus.

In a second aspect of the present invention, there is provided a sequence variant of the A. tubingensis xlnB promoter, characterised in that it possesses at least three copies of the element (SEQ ID NO: 7) CGGCAGGGTCTC. The xylanase B gene is weakly expressed (WO 94/14965) and on account of its being seen as possessing a weak promoter has never been suggested to be a suitable basis for heterologous expression systems. A surprisingly effective sequence variant of the xylanase B promoter, which is particularly strong and suitable for the expression of heterologous nucleotide sequences, has now been isolated and compared to the promoter disclosed in WO 94/14965. The new sequence variant differs from the promoter of WO 94/14965 in the presence of three copies of the element (SEQ ID NO: 7) CGGCAGGGTCTC rather than just two. The presence of the extra element is through to be responsible for the observed increase in transcriptional activation.

The preferred sequence of the variant according to the invention is that of the xlnB promoter as hereinbefore defined shown in SEQ. ID. No. 1, or a variant, homologue or fragnent thereof, provided that the variant, homologue or fragment retains at least three copies of the element according to the invention. The promoter in SEQ. ID. No. 1 is located upstream of the translation start site, and in a preferred embodiment the promoter possesses the sequence as shown between positions 1 and 720 of SEQ. ID. No. 1. Advantageously, the promoter possesses a shorter sequence, preferably that shown between positions 342 and 720 of SEQ. ID. No. 1.

The sequence variant according to the invention may be incorporated in a nucleic acid molecule such that it is operatively linked to a nucleotide sequence. The sequence variant has advantageous properties as a promoter for gene expression, being stronger that the xlnB promoter published in WO 94/14965, and is useful for the expression of a variety of polypeptides, including those encoded by homologous nucleotide sequences such as xylanase B.

The invention is particularly useful in the production of substances useful in the foodstuffs, feed and beverage industries. The preferred host, Aspergillus, is a popular production host in these industries, for the reasons set forth hereinbefore.

The invention moreover provides a method for increasing the level of transcription of a nucleotide sequence from a promoter comprising the steps of inserting at least one heterologous copy of the element (SEQ ID NO: 7) CGGCAGGGTCTC such that it is operably linked to the promoter, and causing the nucleotide sequence to be transcribed.

As used herein, the term "nucleic acid" includes to the natural nucleic acids DNA and RNA, or synthetic nucleic acid analogues which share at least one of the properties of natural nucleic acids, such as the ability to encode a protein or the ability to hybridise to other nucleic acid molecules, preferably natural nucleic acid molecules. The preferred nucleic acid for use in the invention is DNA. Coding sequences may preferably comprise cDNA.

References to the element (SEQ ID NO: 7) CGGCAGGGTCTC according to the present invention include any substitution of, variation of, modification of, replacement of, deletion of or addition of one (or more) nucleotides from or to the sequence providing the resultant nucleotide sequence has the ability to act as an activating element when operatively linked to a promoter in an expression system. In particular, the invention covers homologues of the sequence (SEQ ID NO: 7) CGGCAGGGTCTC as evidenced by relative identity in sequence and/or structure and/or function providing the resultant nucleotide sequence has the ability to act as an activating element according to the invention. With respect to sequence "homology", preferably there is sequence identity of at least 75%, more preferably at least 85%, more preferably at least 90% to the sequence (SEQ ID NO: 7) CGGCAGGGTCTC. More preferably the element of the invention has no more than 1, 2 or 3 nucleotide alterations from the sequence (SEQ ID NO: 7) CGGCAGGGTCTC. Most preferably the element has the sequence (SEQ ID NO: 7) CGGCAGGGTCTC.

The sequences which form part of the present invention may also be in the form of complementary sequences. The term "complementary" means that the present invention also covers nucleotide sequences that can hybridise to the nucleotide sequences of the nucleotide sequence or the promoter sequence, respectively.

The element according to the invention is capable of potentiating transcription from a promoter. This means that, in the presence of the element, the potential for transcription is increased. The promoter may remain subject to other influences, such as tissue specific or nutrient-influenced transcriptional regulation, which may so control the transcription from the promoter that no effect is seen with the addition of the element of the invention. However, when such further influences are neutralised, the element will cause an increase in the level of transcription from the promoter.

The term "construct" is synonymous with terms such as "conjugate", "cassette" and "hybrid". Constructs may be prepared by linking nucleic acid sequences directly or indirectly, according to techniques known in the art. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment.

The term "vector" includes expression vectors and transformation vectors.

The term "expression vector" means a construct capable of in vivo or in vitro expression of a polypeptide gene product encoded by a coding sequence inserted into the vector.

The term "transformation vector" means a construct capable of being transferred from one species to another— such as from an *E. coli* plasmid to a filamentous fungus, preferably of the genus Aspergillus.

As used herein, "vector" refers to discrete elements that are used to introduce heterologous DNA into cells for either expression or replication thereof. Selection and use of such vehicles are known to those skilled in the art. Many vectors are available, and selection of appropriate vector will depend on the intended use of the vector, i.e. whether it is to be used for DNA amplification or for expression, the size of the DNA to be inserted into the vector, and the host cell to be transformed with the vector. Each vector contains various components depending on its function and the host cell for which it is compatible. The vector components generally include, but are not limited to, one or more of the following: an origin of replication, one or more marker genes, an enhancer element, a promoter, a transcription termination sequence and a signal sequence.

Both expression and cloning vectors generally contain at least one nucleic acid sequence that enables the vector to replicate in one or more selected host cells. Typically in cloning vectors, this sequence is one that enables the vector to replicate independently of the host chromosomal DNA, and includes origins of replication or autonomously replicating sequences. Such sequences are well known for a variety of bacteria, yeast and other fungi. The origin of replication from the plasmid pBR322 is suitable for most Gram-negative bacteria, the $2\mu$ plasmid origin is suitable for yeast, and fungal origins may be employed in filamentous fungi, for example the amal replicon (Gems et al., (1991) Gene 98:61–67).

Most expression vectors are shuttle vectors, i.e. they are capable of replication in at least one class of organisms but can be transfected into another organism for expression. For example, a vector is cloned in *E. coli* and then the same vector is transfected into yeast or other fungal cells even though it is not capable of replicating independently of the host cell chromosome. DNA may also be replicated by insertion into the host genome.

Advantageously, an expression and cloning vector may contain a selection gene also referred to as selectable marker which allows for the selection of the genetic construct in, for example, a filamentous fungus, preferably of the genus Aspergillus, such as *Aspergillus niger*, into which it has been transferred. This gene may encode a protein necessary for the survival or growth of transformed host cells grown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from the medium.

As to a selective gene marker appropriate for yeast, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, or HIS3 gene.

Since the replication of vectors is conveniently done in *E. coli*, an *E. coli* genetic marker and an *E. coli* origin of replication are advantageously included. These can be obtained from *E. coli* plasmids, such as pBR322, Bluescript® vector or a pUC plasmid, e.g. pUC18 or pUC19, which contain both *E. coli* replication origin and *E. coli* genetic marker conferring resistance to antibiotics, such as ampicillin.

Moreover, the vector according to the invention preferably includes a secretion sequence in order to facilitate secretion of the polypeptide from hosts, such that it will be produced as a soluble native peptide rather than in an inclusion body.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe based on a sequence provided herein. Those skilled in the art will readily envisage how these methods may be modified, if desired.

The term "host cell", as used herein, includes any cell type, whether a unicellular organism, a cell derived from a multicellular organism and placed in tissue culture or a cell present as part of a multicellular organism, which is susceptible to transformation with a nucleic acid construct according to the invention. Such host cells, such as yeast and higher eukaryote cells, fungal cells and plant cells may be used for replicating DNA and producing polypeptides encoded by nucleotide sequences as used in the invention. Prokaryotic cells are suitable for replicating DNA and include eubacteria, such as Gram-negative or Gram-positive organisms, such as *E. coli*, e.g. *E. coli* K-12 strains, DH5α and HB101, or Bacilli. Host cells suitable for replicating nucleic acids and expressing coding sequences encoded on vectors according to the invention include eukaryotic microbes such as filamentous fungi, e.g. Aspergillus, or yeast, e.g. Saccharomyces.

Particularly preferred are cells from filamentous fungi, preferably Aspergillus, such as *A. niger*, *A. awamori* and *A. tubingensis*.

DNA may be stably incorporated into cells or may be transiently expressed using methods known in the art. Stably transfected cells may be prepared by transfecting cells with an expression vector having a selectable marker gene, and growing the transfected cells under conditions selective for cells expressing the marker gene. To prepare transient transfectants, cells are transfected with a reporter gene to monitor transfection efficiency.

Host cells are transfected or, preferably, transformed with expression or cloning vectors of this invention and cultured in conventional nutrient media modified as appropriate for inducing expression, selecting transformants, or amplifying the genes encoding the desired sequences. Heterologous DNA may be introduced into host cells by any method known in the art, such as transfection with a vector encoding a heterologous DNA by the calcium phosphate coprecipitation technique or by electroporation. Numerous methods of transfection are known to the skilled worker in the field. Successful transfection is generally recognised when any indication of the operation of this vector occurs in the host cell. Transformation is achieved using standard techniques appropriate to the particular host cells used.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g. Sambrook et al. (1989) Molecular Cloning: A Laboratory Manual, Second Edition, Cold Spring Harbor Laboratory Press) and set forth in particular on pages 15 and 16 herein.

Transfected or transformed cells are cultured using media and culturing methods known in the art, preferably under conditions, whereby the polypeptide encoded by the heterologous nucleotide sequence is expressed. The composition of suitable media is known to those in the art, so that they can be readily prepared. Suitable culturing media are also commercially available.

The term "organism" in relation to the present invention includes any organism that could express a nucleotide sequence under the control of the promoter according to the present invention. Organisms in which the molecules according to the invention are expressed are preferably fungal hosts.

Preferably the organism is a filamentous fungus, preferably of the genus Aspergillus, more preferably *A. niger*, *A. awamori* or *A. tubingensis*.

Other preferred organisms include any one of *Aspergillus oryzae, Trichoderma reesei, T. viride* and *T. longibrachiatum*.

The term "transgenic organism" in relation to the present invention includes any organism that comprises the promoter according to the present invention and a nucleotide sequence coding for a heterologous nucleotide sequence, wherein the nucleotide sequence according to the present invention can be expressed within the organism. Preferably the promoter and the nucleotide sequence are incorporated in the genome of the organism.

The term "transgenic organism" does not cover the native nucleotide sequence according to the present invention in its natural environment when it is under the control of its native promoter which is also in its natural environment. In addition, the present invention does not cover the native enzyme according to the present invention when it is in its natural environment and when it has been expressed by its native nucleotide sequence which is also in its natural environment and when that nucleotide sequence is under the control of its native promoter which is also in its natural environment.

The transformed cell or organism may be used to prepare acceptable quantities of the desired compound which may be easily retrievable from the cell or organism.

The term "promoter" is used in the normal sense of the art, e.g. an RNA polymerase binding site in the Jacob-Monod theory of gene expression. Preferably, fungal promoters are used in the present invention. Any suitable promoter may be used in connection with the present invention, with xylan-inducible promoters preferably of fungal origin being especially indicated. A "core" promoter, as referred to herein, in a promoter consisting essentially of a TATA box and a transcriptional initiation site.

Fungal promoters are known in the literature (for example, see Gurr, et al., (1987) The structure and organisation of nuclear genes of filamentous fungi. In Kinghorn, J. R. (ed), Gene Structure in Eukaryotic Microbes, IRL Press, Oxford, pp. 93–139).

In addition to the nucleotide sequences described above, the promoter of the present invention can additionally include features to ensure or to increase expression in a suitable host. For example, the features can be conserved regions such as a TATA box. The TATA box is typically found 30 bp upstream of the transcription initiation site, and is believed to be involved in the assembly of the transcriptional complex.

The promoters may even contain other sequences to affect (such as to maintain, enhance, decrease) the levels of expression of the heterologous nucleotide sequence. Fungal promoters, for instance, typically contain both a TATA box and a UAS (Upstream Activating Site). The UAS is a binding site for the activating regulator acting on the promoter in question. The element of the present invention is believed to be a UAS. Other sites, involved in various aspects of promoter regulation, may also be included.

The element of the invention is, according to the present invention, placed upstream of the promoter. The distance between the promoter and the element may be adjusted, by empirical experimentation, to maximise or adjust the level of transcriptional activation.

The term "heterologous nucleotide sequence" with reference to the constructs according to the present invention means any sequence encoding a polypeptide of interest, other than the complete natural sequence normally associated with the promoter employed, or a sequence which is capable of expressing a nucleic acid, for example a regulatory RNA such as an antisense RNA or a ribozyme, or a tRNA or rRNA capable of regulating the metabolism of an organism. Conversely, the term "nucleotide sequence" includes homologous nucleotide sequences which are the sequences normally associated with the promoters employed. The invention includes the use of both homologous and heterologous nucleotide sequences.

A heterologous nucleotide sequence can be any nucleotide sequence that is either foreign or natural to the organism (e.g. filamentous fungus, preferably of the genus Aspergillus, or a plant) in question. The term "heterologous nucleotide sequence" also includes a homologous nucleotide sequence which has been mutated, such as by insertion, addition, deletion or alteration, such that it is no longer identical with the natural homologous nucleotide sequence.

Typical examples of a heterologous nucleotide sequence include sequences coding for proteins and enzymes that modify metabolic and catabolic processes. The heterologous nucleotide sequence may code for an agent for introducing or increasing pathogen resistance. The heterologous nucleotide sequence may be an antisense construct for modifying the expression of natural transcripts present in the relevant tissues. The heterologous nucleotide sequence may code for a non-native protein of a filamentous fungus, preferably of the genus Aspergillus, or a compound that is of benefit to animals or humans. Examples of nucleotide sequences encoding enzymes include pectinases, pectin depolymerases, polygalacturonases, pectate lyases, pectin lyases, hexose oxidase, oxidoreductases, lipases, glucan lyase, rhamno-galacturonases, hemicellulases, endo-β-glucanases, arabinases, or acetyl esterases, or combinations thereof, as well as antisense sequences thereof. The heterologous nucleotide sequence may be a protein giving nutritional value to a food or crop. Typical examples include plant proteins that can inhibit the formation of anti-nutritive factors and plant proteins that have a more desirable amino acid composition (e.g. a higher lysine content than a non-transgenic plant).

The heterologous nucleotide sequence may code for an enzyme that can be used in food processing such as chymosin, thaumatin, α-galactosidase, a glucanase or β-1, 4-endoglucanase.

The heterologous nucleotide sequence may code for an intron of a particular nucleotide sequence, wherein the intron can be in sense or antisense orientation.

The heterologous nucleotide sequence can be the nucleotide sequence coding for the arabinofuranosidase enzyme which is the subject of PCT patent application PCT/EP96/01009 (incorporated herein by reference). The heterologous nucleotide sequence can be any of the nucleotide sequences coding for the ADP-glucose pyrophosphorylase enzymes which are the subject of PCT patent application PCT/EP94/01082 (incorporated herein by reference). The heterologous nucleotide sequence can be any of the nucleotide sequences coding for the α-glucan lyase enzyme which are described in PCT patent application PCT/EP94/03397 (incorporated herein by reference). The heterologous nucleotide sequence can be any of the sequences coding for T. lanuginosus amylase, as described in PCT patent application PCT/EP95/02607, incorporated herein by reference. The heterologous nucleotide sequence can be any of the nucleotide sequences coding for the glucanase enzyme which are described in PCT patent application PCT/EP96/01008 (incorporated herein by reference). The heterologous nucleotide sequence can be xylanase A or B, as set forth herein.

Preferably the promoter and the nucleotide sequence according to the invention are stably maintained within host cells or transgenic organisms. By way of example, the promoter and/or the nucleotide sequence may be maintained within the transgenic organism in a stable extrachromosomal construct. This is preferred for transgenic yeast or some filamentous fungi. Alternatively, the promoter and/or the heterologous nucleotide sequence (such as the nucleotide sequence according to the present invention) may be stably incorporated within the transgenic organism's genome. This is preferred for some transgenic yeast, and most filamentous fungi.

A preferred host organism for the expression of the nucleic acid constructs of the present invention and/or for the preparation of the heterologous polypeptides according to the present invention is an organism of the genus Aspergillus, such as *Aspergillus niger*. In this regard, a transgenic Aspergillus according to the present invention can be prepared by following the teachings of Rambosek, J. and Leach, J. 1987 (Recombinant DNA in filamentous fungi: Progress and Prospects. CRC Crit. Rev. Biotechnol. 6:357–393), Davis R. W. 1994 (Heterologous gene expression and protein secretion in Aspergillus. In: Martinelli S. D., Kinghorn J. R. (Editors) Aspergillus: 50 years on. Progress in industrial microbiology vol 29. Elsevier Amsterdam 1994. pp 525–560), Ballance, D. J. 1991 (Transformation systems for Filamentous Fungi and an Overview of Fungal Gene structure. In: Leong, S. A., Berka R. M. (Editors) Molecular Industrial Mycology. Systems and Applications for Filamentous Fungi. Marcel Dekker Inc. New York 1991. pp 1–29) and Turner G. 1994 (Vectors for genetic manipulation. In: Martinelli S. D., Kinghorn J. R.(Editors) Aspergillus: 50 years on. Progress in industrial microbiology vol 29. Elsevier Amsterdam 1994. pp. 641–666). The following commentary provides a summary of those teachings for producing transgenic Aspergillus according to the present invention.

For almost a century, filamentous fungi have been widely used in many types of industry for the production of organic compounds and enzymes. For example, traditional Japanese koji and soy fermentations have used Aspergillus sp. Also, in this century *Aspergillus niger* has been used for production of organic acids particular citric acid and for production of various enzymes for use in industry.

There are two major reasons why filamentous fungi have been so widely used in industry. First filamentous fungi can produce high amounts of extracelluar products, for example enzymes and organic compounds such as antibiotics or organic acids. Second filamentous fungi can grow on low cost substrates such as grains, bran, beet pulp etc. The same reasons have made filamentous fungi attractive organisms as hosts for heterologous expression according to the present invention.

In order to prepare the transgenic Aspergillus, expression constructs are prepared by inserting a heterologous nucleotide sequence (such as a nucleotide sequence coding for an amylase enzyme) into a construct designed for expression in filamentous fungi.

Several types of constructs used for heterologous expression have been developed. The constructs contain the promoter according to the present invention which is active in fungi. The heterologous nucleotide sequence can be fused to a signal sequence which directs the protein encoded by the heterologous nucleotide sequence to be secreted. Usually a signal sequence of fungal origin is used. A terminator active in fungi may also be employed.

Another type of expression system has been developed in fungi where the heterologous nucleotide sequence is fused to a fungal gene encoding a stable protein. This can stabilise the protein encoded by the heterologous nucleotide sequence which encodes a protein of interest (POI). In such a system a cleavage site, recognised by a specific protease, can be introduced between the fungal protein and the protein encoded by the heterologous nucleotide sequence, so the produced fusion protein can be cleaved at this position by the specific protease thus liberating the protein encoded by the heterologous nucleotide sequence. By way of example, one can introduce a site which is recognised by a KEX-2 like peptidase found in at least some Aspergilli (Broekhuijsen et al 1993 J Biotechnol 31 135–145). Such a fusion leads to cleavage in vivo resulting in protection of the expressed product and not a larger fusion protein (see U.S. Pat. No. 5,679,543).

Heterologous expression in Aspergillus has been reported for several genes coding for bacterial, fungal, vertebrate and plant proteins. The proteins can be deposited intracellularly if the nucleotide sequence according to the present invention (or another heterologous nucleotide sequence) is not fused to a signal sequence. Such proteins will accumulate in the cytoplasm and will usually not be glycosylated which can be an advantage for some bacterial proteins. If the nucleotide sequence according to the present invention (or another heterologous nucleotide sequence) is equipped with a signal sequence the protein will accumulate extracelluarly.

With regard to product stability and host strain modifications, some heterologous proteins are not very stable when they are secreted into the culture fluid of fungi. Most fungi produce several extracelluar proteases which degrade heterologous proteins. To avoid this problem special fungal strains with reduced protease production have been used as host for heterologous production.

For the transformation of filamentous fungi, several transformation protocols have been developed for many filamentous fungi (Ballance, D. J. 1991 (Transformation systems for Filamentous Fungi and an Overview of Fungal Gene structure. In: Leong, S. A., Berka R. M. (Editors) Molecular Industrial Mycology. Systems and Applications for Filamentous Fungi. Marcel Dekker Inc. New York 1991. pp 1–29). Many of them are based on preparation of protoplasts and introduction of DNA into the protoplasts using PEG and $Ca^{2+}$ ions. The transformed protoplasts then regenerate and the transformed fungi are selected using various selective markers. Among the markers used for transformation are a number of auxotrophic markers such as argB, trpC, niaD and pyrG, antibiotic resistance markers such as benomyl resistance, hygromycin resistance and phleomycin resistance. A commonly used transformation marker is the amdS gene of *A. nidulans* which in high copy number allows the fungus to grow with acrylamide as the sole nitrogen source.

In another embodiment the transgenic organism can be a yeast. In this regard, yeast have also been widely used as a vehicle for heterologous gene expression. The species *Saccharomyces cerevisiae* has a long history of industrial use, including its use for heterologous gene expression. Expression of heterologous genes in *Saccharomyces cerevisiae* has been reviewed by Goodey et al (1987, Yeast Biotechnology, D R Berry et al, eds, pp 401–429, Allen and Unwin, London) and by King et al (1989, Molecular and Cell Biology of Yeasts, E F Walton and G T Yarranton, eds, pp 107–133, Blackie, Glasgow).

For several reasons *Saccharomyces cerevisiae* is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae*.

A review of the principles of heterologous gene expression in *Saccharomyces cerevisiae* and secretion of gene products is given by E Hinchcliffe E Kenny (1993. "Yeast as a vehicle for the expression of heterologous genes", Yeasts, Vol 5, Anthony H Rose and J Stuart Harrison, eds, 2nd edition, Academic Press Ltd.).

Several types of yeast vectors are available, including integrative vectors, which require recombination with the host genome for their maintenance, and autonomously replicating plasmid vectors.

In order to prepare the transgenic Saccharomyces, expression constructs are prepared by inserting a nucleotide sequence comprising a DNA construct according to the present invention into a construct designed for expression in yeast. Several types of constructs used for heterologous expression have been developed, suitable component parts of which are discussed hereinbefore.

For the transformation of yeast several transformation protocols have been developed. For example, a transgenic Saccharomyces according to the present invention can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153, 163–168).

The following sequences are set forth in the Sequence Listing:

| | |
|---|---|
| SEQ. ID. No. 1 | *A. tubingensis* Xylanase B |
| SEQ. ID. No. 2 | *A. tubingensis* Xylanase B amino acid sequence |
| SEQ. ID. No. 3 | The *A. tubingensis* Xylanase B promoter region |
| SEQ. ID. No. 4 | The Xylanase A gene |
| SEQ. ID. No. 5 | The amyA gene |
| SEQ. ID. No. 6 | The complete nucleotide sequence of pPR70 |
| SEQ. ID. No. 7–15 | Synthetic DNA oligonucleotide primers |

Deposition Data

The following deposits have been made under the Budapest Treaty in connection with the present application at the NCIMB, 23 St. Machar Drive, Aberdeen, AB2 1RY, Scotland:

| | | |
|---|---|---|
| *E. coli* DH5α pXylA | Accession No. 40861 | Deposited 20.2.1997 |
| *E. coli* DH5α pXylB | Accession No. 40862 | Deposited 20.2.1997 |
| *E. coli* DH5α pxlnB-AmyA | Accession No. 40858 | Deposited 31.1.1997 |

The invention is described hereinbelow, for the purposes of illustration only, with reference to the following examples, in which reference is made to the following figures.

FIG. 11 shows the alignment of Ppr70 and variants among the xlnB elements. The start of the sequences is the SnaBI site (5661) into which the elements are inserted.

EXAMPLE 1

Preparation of xlnB-amyA-xlnA Construct

Figure 1:
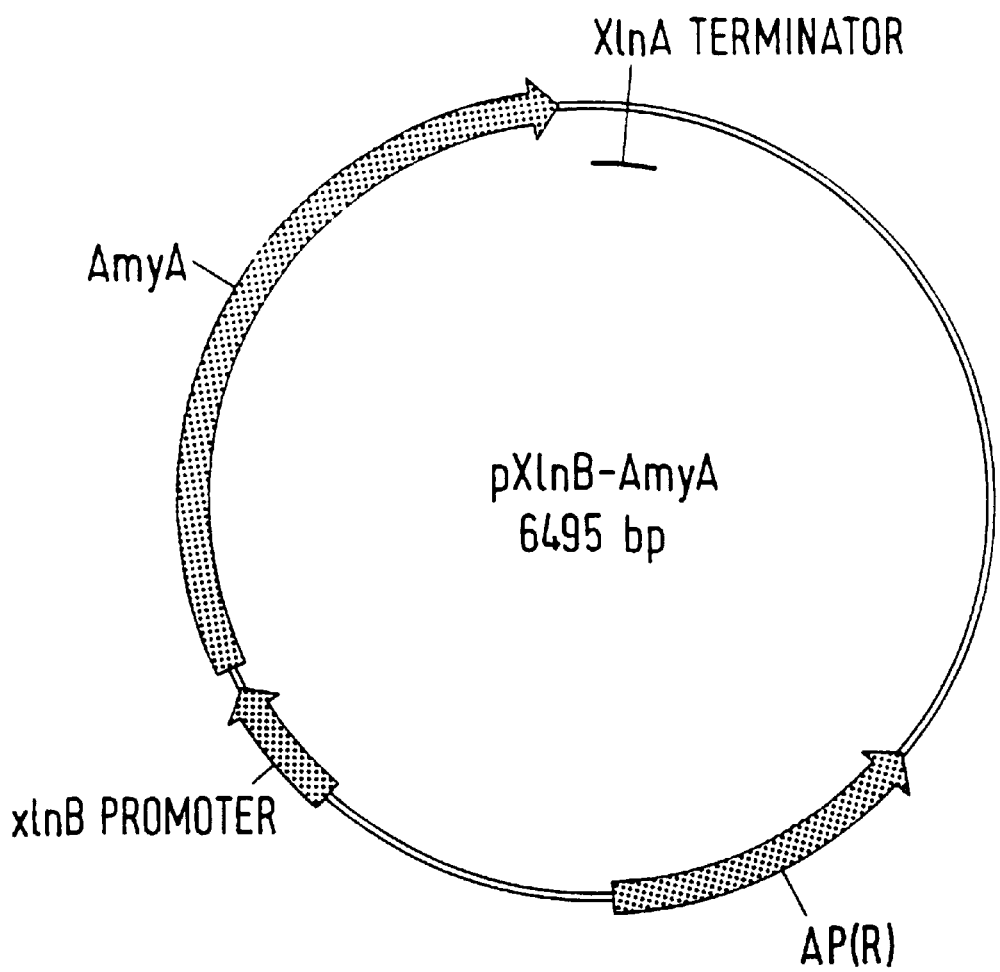
FIG. 1 shows plasmid pxlnB-AmyA, which comprises the xlnB promoter, the amyA gene and the xlnA terminator, together with an ampicillin resistance selection marker.

Basic molecular manipulation is performed according to established techniques such as those described in: J. Sambrook, et al., Molecular Cloning, A Laboratory Manual. Second Edition, Cold Spring Harbour Press, New York 1989. Restriction enzymes are used according to the instructions supplied by the manufacturer (New England Biolabs Ltd. and Amersham Ltd.)

pXYLA containing the xlnA gene (SEQ. ID. No. 4) is digested with BamnHI and XbaI and the 1081 bp fragment containing the xlnA terminator is purified and inserted into a BamHI-XbaI digested pBluescriptIISK+ vector. The resulting vector is called pPR15.

pXYLB containing the entire xlnB gene (SEQ. ID. No. 1) is digested with NspI and blunt ended with Mung Bean Nuclease. The nuclease is inactivated by heat treatment 15 min 65° C., whereafter the DNA is digested with ClaI, and a fragment of 377 bp containing the xlnB promoter is purified.

pPR15 is digested with EcoRI and the postruding ends are completely filled in using Klenow polymerase. The enzyme is heat inactivated 15 min 75° C., and the vector digested with ClaI. The purified promoter is inserted into the digested vector and the resulting plasmid pPR42 is obtained.

pAMYA-3 (See PCT/EP95/02607; deposited under accession no. NCIMB 40657) containing amyA (SEQ. ID. No. 5), encoding the α-amylase of *T. lanuginosus* is digested with ScaI and Ecl136II and a 2106p fragment containing the complete amyA gene is purified and inserted into pPR42 digested with SmaI and dephosphorylated with Calf Intestinal phosphatase. A transforming with the correct orientation of the gene is identified by restriction analysis and the resulting plasmid is named pxlnB-AmyA (FIG. 1)

The xlnB promoter corresponds to nucleotide 342–720 of the sequence in SEQ. ID. No. 1.

The amyA gene corresponds to nucleotide 406–2512 of the sequence in SEQ. ID. No. 5.

The xlnA terminator corresponds to nucleotide 1883–2962 of the sequence in SEQ. ID. No. 4.

EXAMPLE 2

Transformation of the Construct in *Aspergillus awamori*

The xlnB-amyA-xlnA construct is transformed into *A. awamori*, generally obtainable from the ATCC under accession no. 11358, by the following protocol (see also WO 96/29415) using cotransformation with a Hygromycin resistance marker (Werners, K. et al (1987) Molecular and General Genetics 209, 71–77).

The protocol for transformation of *A. awamori* is based on the teachings of Buxton, F. P., Gwynne D. I., Davis, R. W. 1985 (Transformation of *Aspergillus niger* using the argB gene of *Aspergillus nidulans*. Gene 37:207–214), Daboussi, M. J., Djeballi, A., Gerlinger, C., Blaiseau, P. L., Cassan, M., Lebrun, M. H., Parisot, D., Brygoo,Y. 1989 (Transformation of seven species of filamentous fungi using the nitrate reductase gene of *Aspergillus nidulans*. Curr. Genet. 15:453456) and Punt, P. J., van den Hondel, C.A.M.J.J. 1992 (Transformation of filamentous fungi based on hygromycin B and Phleomycin resistance markers. Meth. Enzym. 216:447–457).

For the purification of protoplasts, spores from one PDA (Potato Dextrose Agar—from Difco Lab. Detroit) plate of fresh sporulated N400 (CBS 120.49, Centraalbureau voor Schimmelcultures, Baarn) (7 days old) are washed off in 5–10 ml water. A shake flask with 200 ml Potato Dextrose Broth (Difco 0549-17-9, Difco Lab. Detroit) is inoculated with this spore suspension and shaken (250 rpm) for 16–20 hours at 30° C.

The mycelium is harvested using Miracloth (Nylon® mesh) and 3–4 g wet mycelium are transferred to a sterile petri dish with 10 ml STC (1.2 M sorbitol, 10 mM Tris HCl pH 7.5, 50 mM $CaCl_2$) with 75 mg lysing enzymes (Sigma L-2265) and 4500 units lyticase (Sigma L-8012).

The mycelium is incubated with the enzyme until the mycelium is degraded and the protoplasts are released. The degraded mycelium is then filtered through a sterile 60 $\mu$m mesh filter. The protoplasts are harvested by centrifugation 10 min at 2000 rpm in a swing out rotor. The supernatant is discarded and the pellet is dissolved in 8 ml 1.5 M $MgSO_4$ and then centrifuged at 3000 rpm for 10 min.

The upper band, containing the protoplasts is transferred to another tube, using a transfer pipette and 2 ml 0.6 M KCl is added. Carefully 5 ml 30% sucrose is added on the top and the tube is centrifuged 15 min at 3000 rpm.

The protoplasts, lying in the interface band, are transferred to a new tube and diluted with 1 vol. STC. The solution is centrifuged 10 min at 3000 rpm. The pellet is washed twice with STC, and finally solubilised in 1 ml STC. The protoplasts are counted and eventually concentrated before transformation.

For the transformation, 100 $\mu$l protoplast solution ($10^6$–$10^7$ protoplasts) are mixed with 10 $\mu$l DNA solution containing 5–10 $\mu$g DNA and incubated 25 min at room temperature. Then 60% PEG-4000 is carefully added in portions of 200 $\mu$l, 200 $\mu$l and 800 $\mu$l. The mixture is incubated 20 min at room temperature. 3 ml STC is added to the mixture and carefully mixed. The mixture is centrifuged 3000 rpm for 10 min.

The supernatant is removed and the protoplasts are solubilised in the remaining of the supernatant. 3–5 ml top agarose is added and the protoplasts are quickly spread on selective plates. Transformed colonies subsequently picked and grown up as set forth below.

EXAMPLE 3

Analysis of Transformants

Hygromycin resistant transformants are grown in minimal medium containing basal inorganic salts, 0.5% glucose, 0.5% oat spelt xylan and 50 mM MES pH 6.0, at 30° C. shaking 250 rpm. After 5 days of growth culture samples are analyzed for alpha-amylase using the CERALPHA substrate (alpha-amylase measuring kit) (MegaZyme, Australia). One vial of CERALPHA is dissolved in 10 ml water to get the useable substrate. The analysis is performed in microtiter wells. In each well 175 ul buffer (50 mM Citrate buffer pH 6.2, 5 mM $CaCl_2.2H_2O$), 25 ul sample (diluted in buffer if necessary) and 50 ul CERALPHA substrate is mixed and the reaction mixture is incubated 15 min at 37° C. The reaction is stopped by transferring 100 ul of the reaction to 1.50 ul 1% Trizma base in a new microtiter well. Activity is measured as a rise in $OD_{420}$ measured in an Elisa reader.

The best producing transformants are grown in shake flasks in a medium composed of 2% beet pulp, 2% wheat bran, 0.3% $NaNO_3$, 100 mM MES pH 5.5. The cultures are grown for 5–7 days at 30° C. with shaking 250 rpm.

Figure 2:
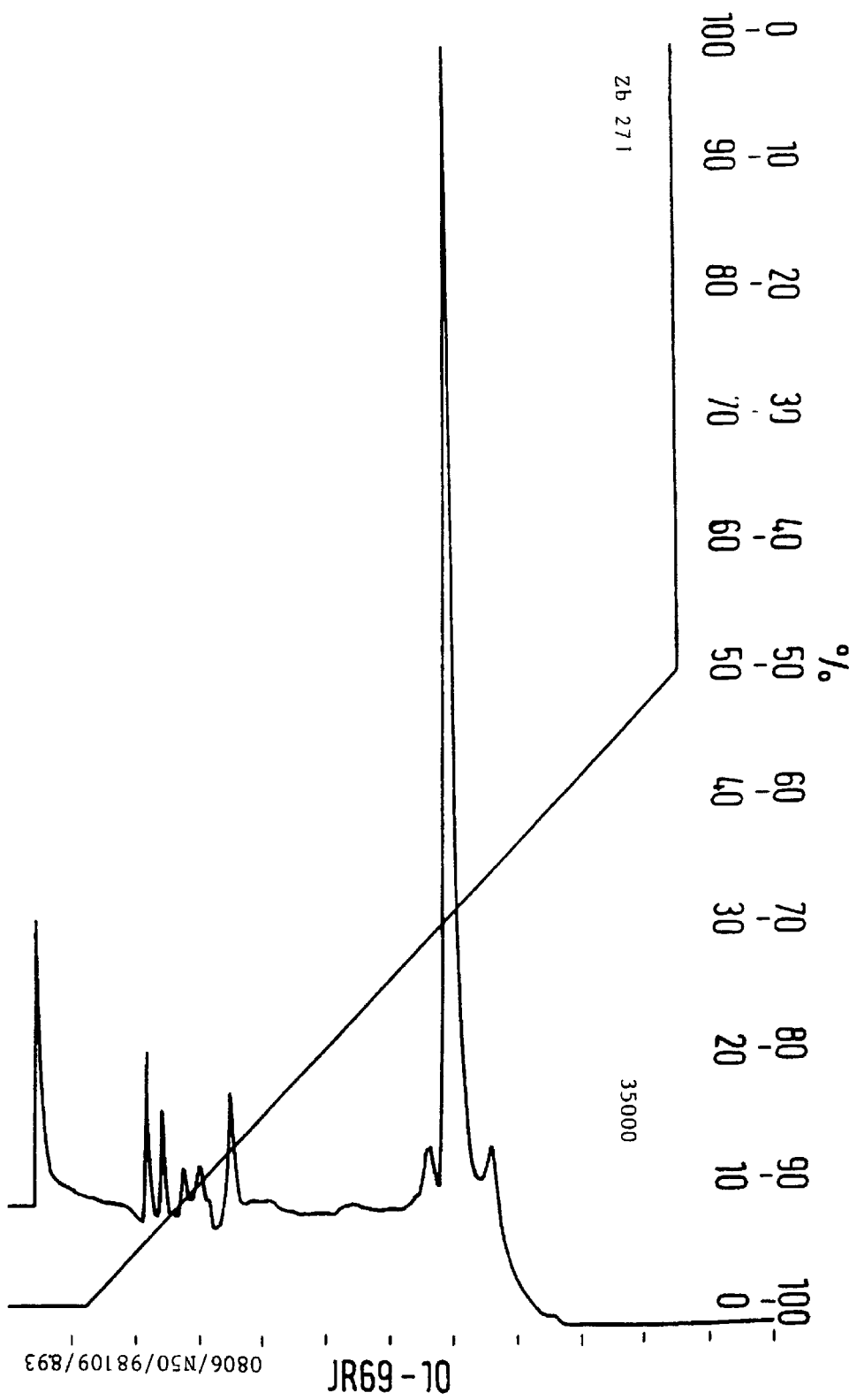
FIG. 2 shows a mono-Q chromatogram of the culture broth of *A. niger* transformed with pxlnB-AmyA.
Figure 3:
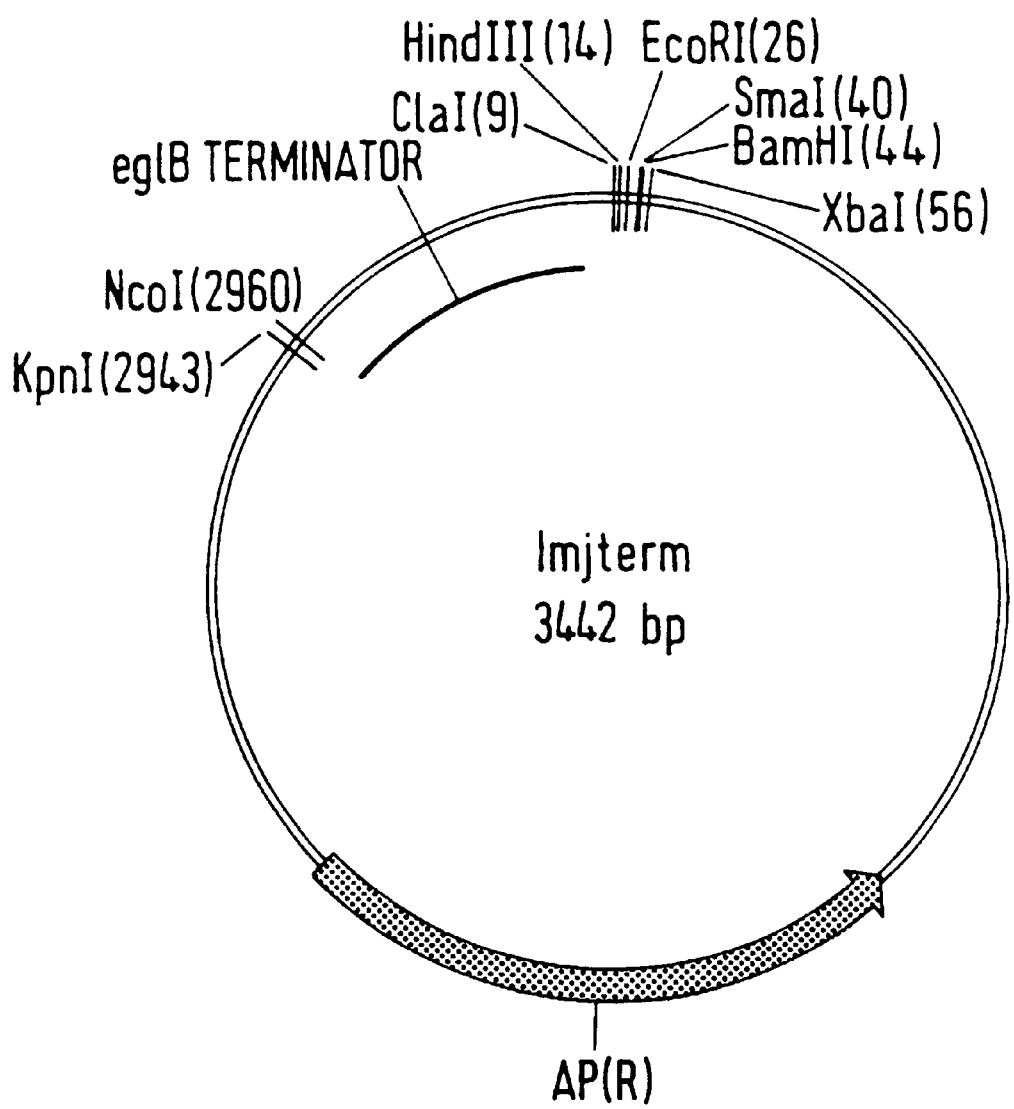
FIG. 3 shows plasmid LMJterm.
Figure 4:
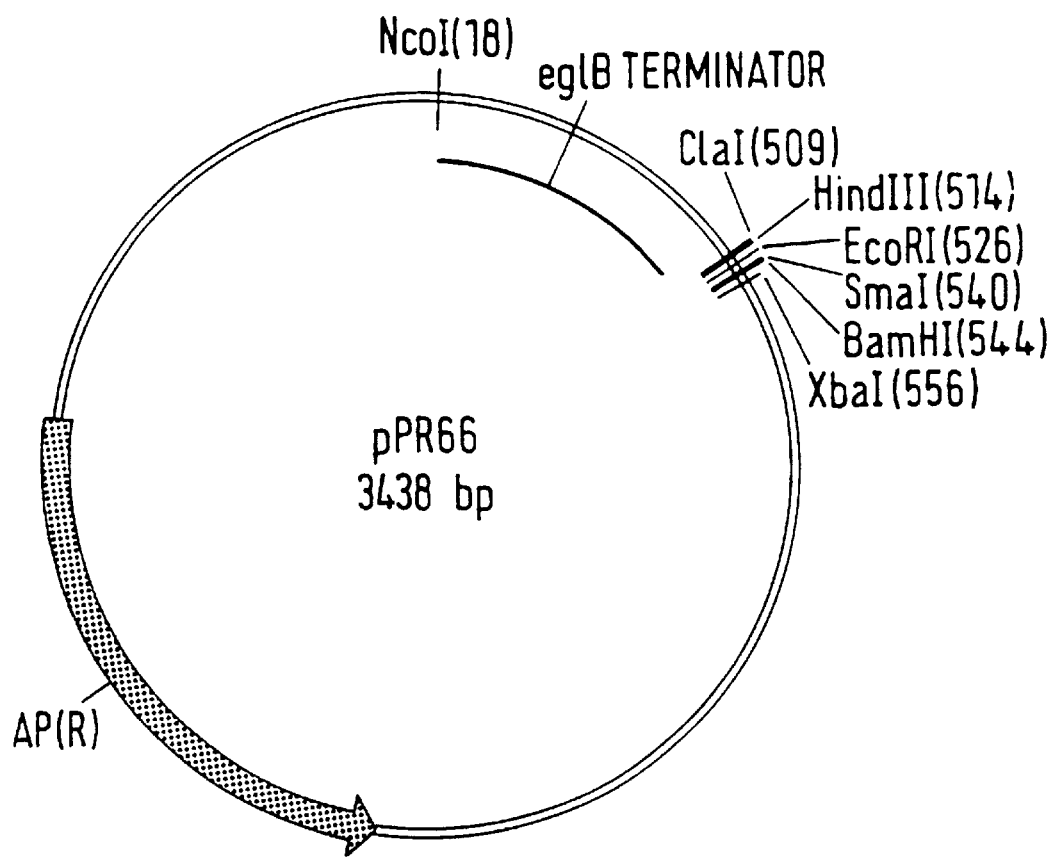
FIG. 4 shows plasmid pPR66.
Figure 5:
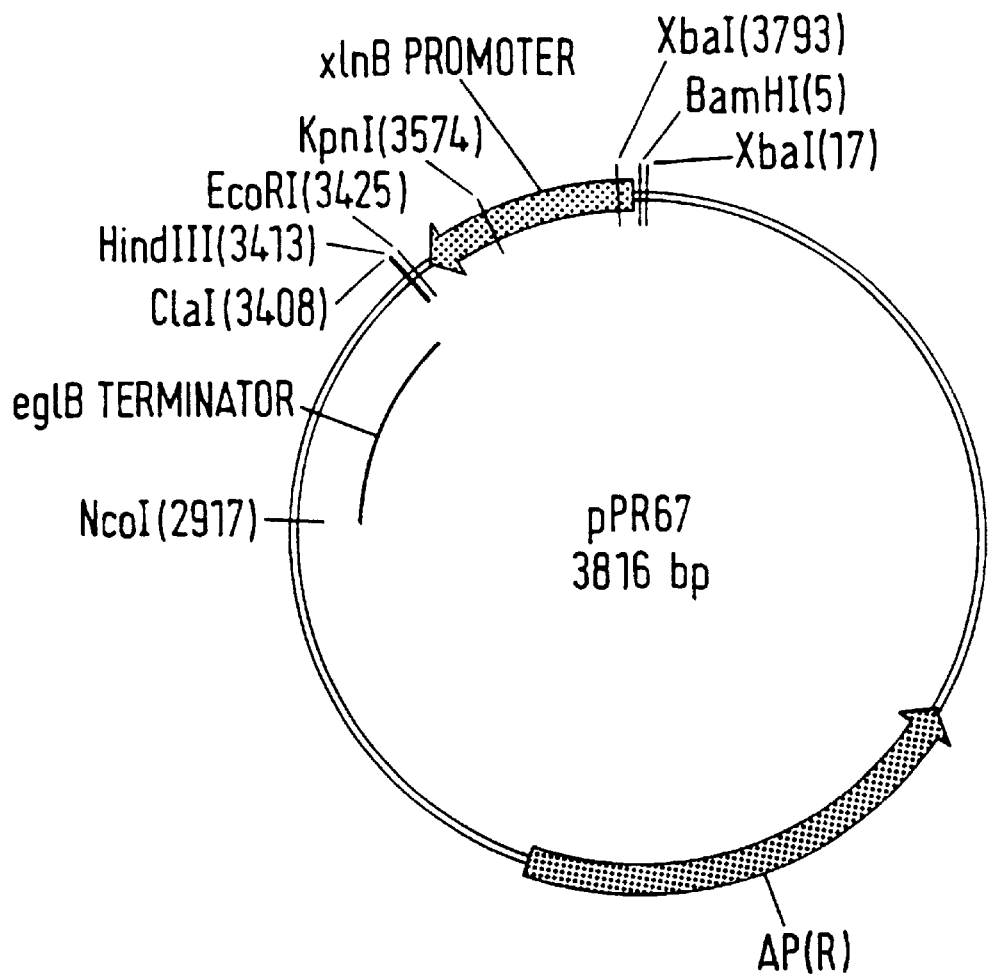
FIG. 5 shows plasmid pPR67.
Figure 6:
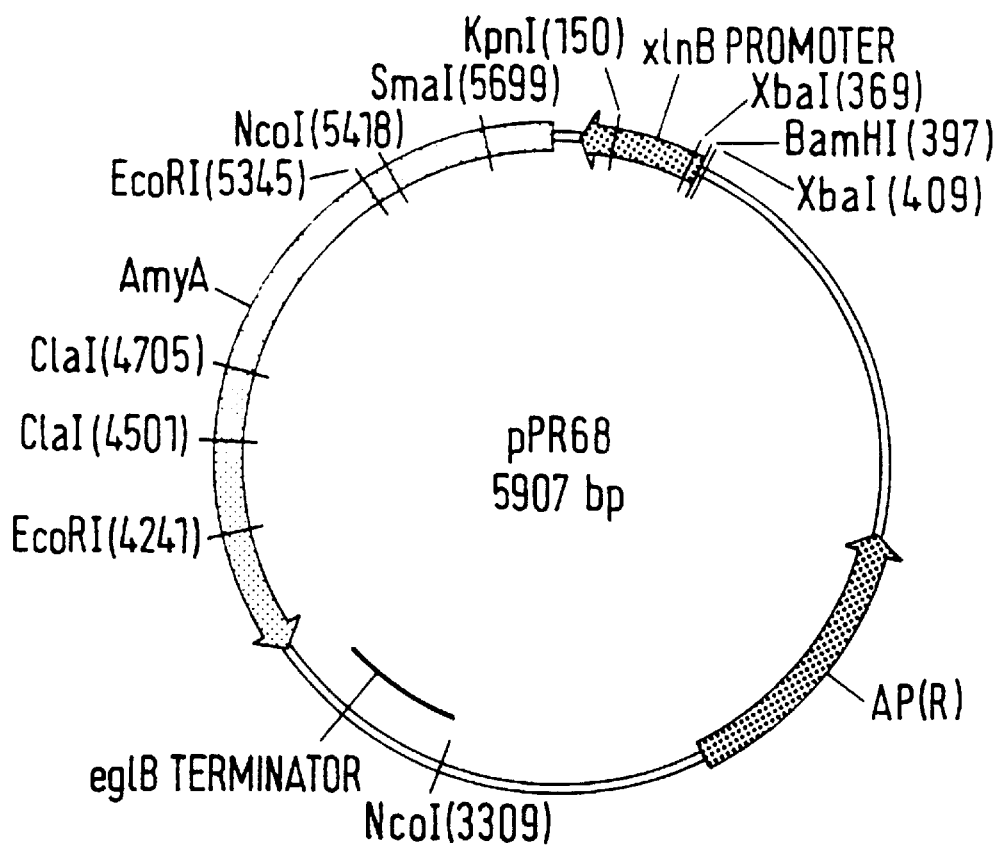
FIG. 6 shows plasmid pPR68.
Figure 7:
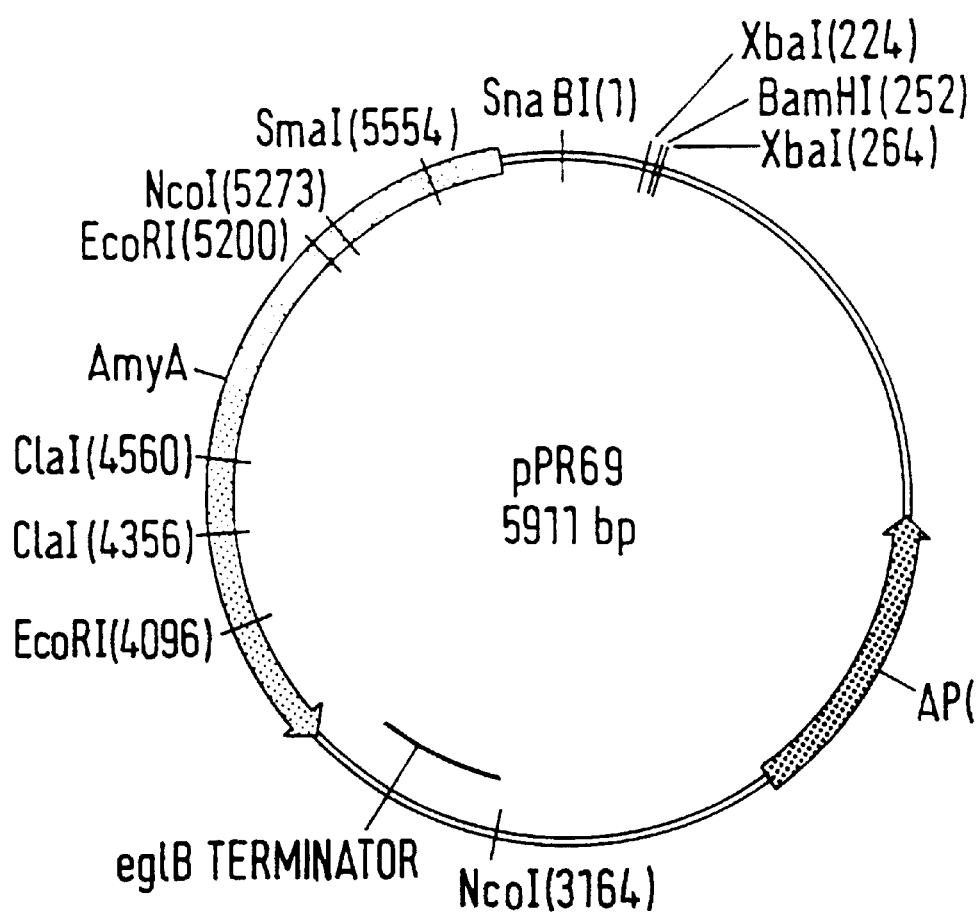
FIG. 7 shows plasmid pPR69.
Figure 8:
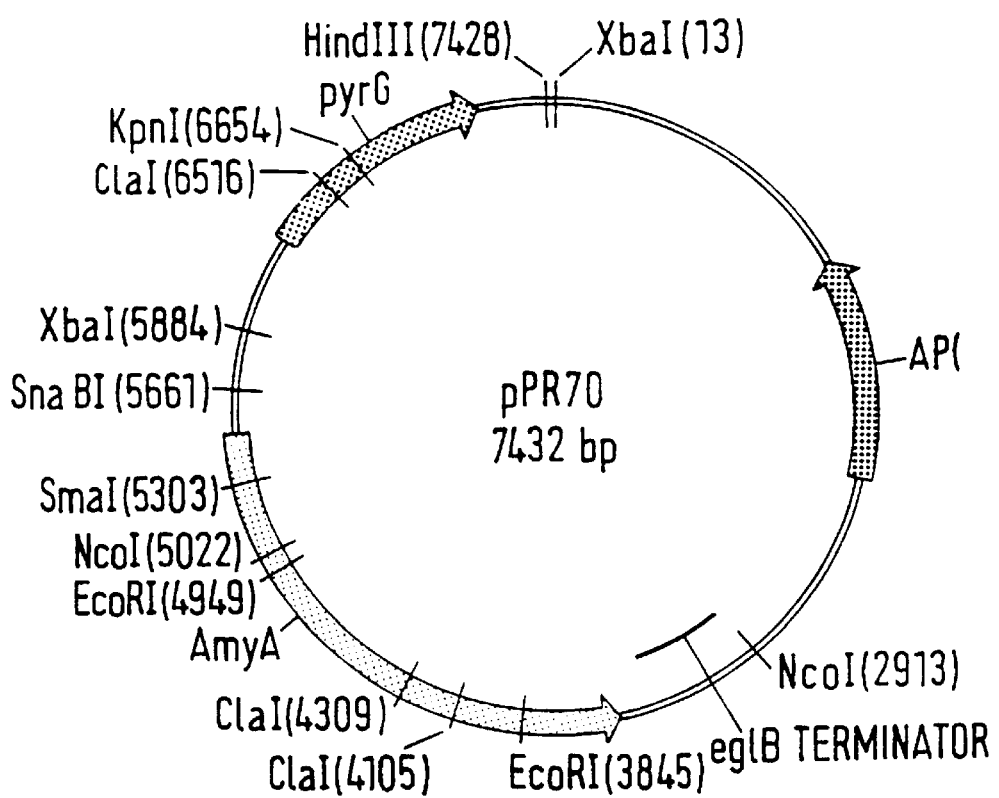
FIG. 8 shows plasmid pPR70.

The activity is measured and surprisingly more than 1 g/l of *T. lanuginosus* α-amylase is obtained. A Mono-Q chromatogram is shown in FIG. 2, and was performed as follows. A sample of a culture broth in which a transformant organism has been grown is filtered through a 0.45 $\mu$m filter. 1.5 ml of the filtrate is applied to a PD-10 column (Pharmacia, Sweden) equilibrated with 10 mM triethanotamine pH 7.0 (Buffer A), and eluted with 2.5 ml Buffer A. 1 ml of the eluate is loaded on a Mono-Q HR5/5 column (Pharmacia) equilibrated with Buffer A. The column is washed with Buffer A until the base line is stable. The proteins bound to the column are than eluted using a salt gradient of 0 to 0.5M NaCl in Buffer A. The eluted proteins are detected at $OD_{280}$.

EXAMPLE 4

Construction of an Expression Vector Containing the xlnB Promoter

A vector for analysis of the xlnB promoter is constructed as follows. The vector pLMJterm containing a fungal terminator in a pBluescriptSKII+ (Stratagene), which is constructed by inserting the egl B gene terminator fragment located between positions 2330 and 2823 of SEQ. ID. No. 16 of PCT/EP97/04415 (derived from GB 9617184.8, published Feb. 15, 1998) into pBluescript, is digested with KpnI. The extensions are removed using T4 DNA polymerase and following the blunt ended vector is religated to give the plasmid pPR66.

pXYLB is digested with ClaI and NspI and a fragment of 382 nucleotides containing the xlnB promoter is purified. This fragment is treated with T4 DNA polymerase to remove extensions and subsequently ligated into pPR66, digested with SmaI and dephosphorylated using calf intestinal phosphatase. Plasmids are purified from transformants and digested with XbaI to isolate the desired plasmid where the xlnB promoter transcribes towards the terminator. Such a plasmid is isolated and named pPR67. This plasmid is an expression vector containing the xlnB promoter and a functional fungal terminator.

In order to insert a reporter gene in the expression vector, pAMYA-1 (WO 96/01323) is digested with ScaI and Ecl136II and a fragment of 2106 nucleotides comprising the amyA gene is purified, as in Example 1. pPR67 is digested with ClaI and EcoRI, blunt-ended using Klenow polymerase, and dephosphorylated using Calf intestinal phosphatase. The purified fragment containing amyA is ligated into pPR67 treated in this manner. A recombinant plasmid with the amyA gene in the correct orientation is found by restriction analysis using NcoI. This plasmid is named pPR68.

pPR68 is a expression vector with the xlnB promoter controlling the expression of α-amylase from amyA. In the xlnB promoter a unique KpnI site is located in which additional copies of the xlnB element can be inserted.

Next a selective marker gene pyrG is inserted into the vector. Unfortunately this gene contains a KpnI site which means that the KpnI site in the promoter will not be unique. Therefore the KpnI site of pPR68 is converted into a SnaBI site. pPR68 is digested with Acc65I (which recognises the same site as KpnI but give 5' extension ends instead of 3' extension ends) and the ends are filled in using Klenow polymerase. The vector is religated and the KpnI site is converted into a SnaBI Site. This vector is called pPR69.

Finally, a pyrG selection marker is inserted into the plasmid. A XbaI-HindIII fragment of 1517 nucleotides is purified from pAB4-1 (van Hartingsveldt et al., Mol. Gen. Genet. (1987) 206: 71–75). The fragment is treated with Klenow polymerase in order to blunt the ends. pPR69 is digested with BamHI and treated with Klenow polymerase. The purified and modified fragment is ligated into the digested and treated vector, and a recombinant vector called pPR70 is isolated.

pPR70 is the desired expression vector. It contains a reporter gene amyA under control of the xlnB promoter, a unique SnaBI site is convenient located in the promoter into which additional copies of the xlnB element can be inserted, and finally a selection marker pyrG is included which allows integration of the plasmid and variants into the pyrG locus which makes the comparison more reliable. The complete sequence of pPR70 is given in SEQ. ID. No. 6.

EXAMPLE 5
Construction of Expression Vectors Containing Derivatives of the xlnB Promoter The following oligonucleotides are synthesised on a Applied Biosystems 392 DNA/RNA synthesiser:

sense CGG CAG GGT CTC (SEQ. ID. No. 7)

antisense GAG ACC CTG CCG (SEQ. ID. No. 8)

Annealing of oligonucleotides: 100 pmol of each oligonucleotide is mixed in a tube in a total volume of 20 μl. The tube is heated for 2 min at 70° C. and allowed to cool slowly to room temperature. The annealed oligonucleotides are stored at −20 and kept on ice at use.

5 pmol of the annealed oligonucleotide is ligated with approximately 100 ng pPR70 digested with SnaBI. After ligation the reaction is digested with SnaBI to avoid pPR70 from religating without insert. Transformants which have lost the SnaBI site are analysed by sequencing.

The following primer is designed for sequencing: TCG ACT GAG CTT TCC ACT CAT (SEQ. ID. No. 9). The primer is Cy5 labelled in the 5' end to be used for sequencing in an ALF sequencer (Pharmacia). The primer binds to the amyA gene (position 5407–5427 in pPR70) and sequencing from the primer reads through the xlnB promoter.

By sequencing, a number of derivatives of pPR70 with modified number of xlnB copies are identified:

pPR70 tacgtacctgccGAGACCCTGCCGAGAC-CCTGCCGaggccctaaatgtGAGACCCTGCCGtac (SEQ. ID. No. 10)

pPR70-6 tacGAGACCCTGCCGaggccctaaatgt-GAGACCCTGCCGtac (SEQ. ID. No. 11)

pPR70-16 tacGAGACCCTGCCGAGACCCTGCCGag-gccctaaatgtGAGACCCTGCCGtac (SEQ. ID. No. 12)

pPR70-3 tacGAGACCCTGCCGgtacctgc-cGAGACCCTGCCGAGACCCTGCCGaggc-cctaaatgtGAGACCCTGCCGtac (SEQ. ID. No. 13)

pPR70-5 tacGAGACCCTGCCGGAGACCCTGCCGg-tacctgccGAGACCCTGCCGAGACCCT-GCCGaggccctaaatgtGAGACCCTGCCGtac (SEQ. ID. No. 14)

pPR70-4 tacGAGACCCTGCCGCGGCAGGGTCTC-CGGCAGGGTCTCgtacctgccGAGAC-CCTGCCGAGACCCTGCCGaggc-cctaaatgtGAGACCCTGCCGtac (SEQ. ID. No. 15)

The lowercase letters represent the sequences between the xlnB elements. The uppercase letters are the xlnB elements. Note that due to the positioning of the sequencing primer site, the sequences are derived from the − strand. An alignment of the complementary (+ strand) sequences, which correspond to the sequences shown in the SEQ. IDs., is shown in Table 1. All the sequences start at the SnaBI site of pPR70 (position 5661) or the corresponding site in which additional elements have been inserted. In the constructs where a deletion is observed is the most likely explanation is that an element has inserted, and a recombination event has subsequently occurred between two xlnB elements where some nucleotides have been lost, creating the observed deletions.

The variants can be described in the following way:

pPR70-6 a xlnB element has been deleted as well as 9 nucleotides next to the elements. Only two elements are retained in this plasmid.

pPR70-16 9 nucleotides next to xlnB elements have been deleted. Three elements are in this construct.

pPR70-3 one xlnB element has been added so that four xlnB elements are present in this construct.

pPR70-5 two elements have been added giving five xlnB elements in this construct.

pPR70-4 Three elements have been added. Of these one is in the same orientation as the native xlnB elements. The other two are in the opposite orientation.

EXAMPLE 6
Transformation of the Constructs in *Aspergillus niger*

Plasmid pPR70 and its derivatives are transformed into *A. niger* AB6-4, obtained from Dr. P. Punt, Netherlands Organisation for Applied Scientific Research (TNO), Nutrition and Food research Institute, Biochemistry and Gene Technology, Zeist, The Netherlands, by the following protocol (see also WO 96/29415).

The protocol for transformation of *A. niger* is based on the teachings of Buxton, F. P., Gwynne D. I., Davis, R. W. 1985 (Transformation of *Aspergillus niger* using the argB gene of *Aspergillus nidulans*. Gene 37:207–214), Daboussi, M. J., Djeballi, A., Gerlinger, C., Blaiseau, P. L., Cassan, M., Lebrun, M. H., Parisot, D., Brygoo,Y. 1989 (Transformation of seven species of filamentous fungi using the nitrate reductase gene of *Aspergillus nidulans*. Curr. Genet. 15:453–456) and Punt, P. J., van den Hondel, C.A.M.J.J. 1992 (Transformation of filamentous fungi based on hygromycin B and Phleomycin resistance markers. Meth. Enzym. 216:447–457).

*Aspergillus niger* AB6-4 (pyrG, ΔglaA, fwnA) is used as the expression host. AB6-4 is grown on Potato dextrose agar (PDA, Difco Labs. Detroit) for 5–7 days until the conidia are formed. Conidia are then washed form the culture with 10 ml ST (0.8% Sodium chloride, 0.05% Tween-20). A 500 ml shake flask containing 200 ml rich medium is inoculated with $10^6$ conidia/ml and grown for 20 h at 30° C. with shaking.

The mycelium is harvested and washed with 1% NaCl, approximately 1 g wet weight mycelium is transferred to a 300 ml shake flask together with 20 ml SMC (1.33M Sorbitol, 50 mM $CaCl_2$, 20 mM MES buffer pH 5.8) and 150 mg lysine enzyme (Sigma no. L2265) and incubated at 37° C. until protoplasts are released (1–3 hours).

Protoplasts are purified by filtration through glass wool in a 20 ml syringe. In this filtration the protoplasts passes through the glass wool filter, whereas the mycelium debris remains in the filter.

The enzymatic solution containing protoplasts is centrifuged at 2500 rpm for 10 min in a Hettisch universal 30 F centrifuge. The pellet containing the protoplast is then dispersed in 10 ml STC (1.33 M Sorbitol, 50 mM $CaCl_2$, 10 mM Tris.HCl pH 7.5) and centrifuged again. This wash is repeated. Finally the protoplasts are dispersed in 1 ml STC and counted. The protoplast suspension is diluted with STC to a final concentration of $5\times10^7$ protoplasts per ml.

To transform the protoplasts 100 $\mu l$ protoplast suspension is mixed with 1–10 $\mu g$ plasmid DNA and incubated for 25 min at room temperature. Aliquots of 200, 200 and 850 $\mu l$ PEG buffer (60% PEG-4000, 10 mM Tris.HCl, 50 mM $CaCl_2$) are added, and after each addition the mixture is carefully mixed. The mixture is then incubated for 20 min at room temperature.

The protoplasts are then washed 2–3 times with 8 ml STC and finally dispersed into approximately 0.5 ml STC.

4 ml melted top agarose, prepared to the same formulation as the selective plates (see below) but employing 0.6% agarose in place of agar, cooled to 46° C., is added to the 0.5 ml suspension and the mixture is immediately poured onto selection plates for selection of transformants.

After incubation for 4–6 days at 30° C. transformants emerge and are recultivated on minimal plates.

Rich Medium is prepared in the following way:

| per liter: | 100 ml | Basal salt solution |
| --- | --- | --- |
| | 1 ml | Trace element solution (Vishniak's solution: Vishniac, W. and Santer M. (1957) The Thiobaccilli. Bacteriol. Rev. 21:195–213) |
| | 10 ml | 1M $(NH_4)_2SO_4$ |

After autoclaving 200 ml is transferred to a 500 ml sterile shake flake and 20 ml 20% glucose, 20 ml 2% casein hydrolysate and 10 ml 5% yeast extract is added, under sterile conditions.

Selective plates per liter

| 100 ml | Basal salt solution |
| --- | --- |
| 1 ml | Trace element solution (Vishniak's solution) |
| 10 ml | 1M $(NH_4)_2SO_4$ |
| 219 g | Sorbitol (= 1.2 mol) |
| 20 g | glucose (Can be omitted when sorbitol is present) |
| 20 g | agar |

The solution for autoclaved 20 min at 120° C., cooled to 60° C. and poured into petri dishes.

Minimal plates are prepared in the same by but without sorbitol.

Basal Salt solution, per liter:

5g KCl 5 g $MgSO_4$ $7H_2O$ 15 g $NaH_2PO_4$ 1 g $CaCl_2$

EXAMPLE 7

Determination of Integration Locus and Copy Number

Total DNA is extracted from the transformants by the following procedure: Approximately 0.5 g mycelium is harvested and transferred to an Eppendorf tube. 200 ul glass beads (diameter 1 mm) and 0.5 ml extraction buffer (100 mM tris-HCl pH 8.0, 50 mM disodium ethylene diamino tetraacetate (EDTA), 500 mM NaCl 1 mM dithiothreitol) is added and the mycelium is homogenized for 30 s in a MINI BEAD BEATER agitator (Biospec Inc.).

50 $\mu l$ 20% SDS (sodium dodecylsulphate) is added and the tubes are incubated for 10 min at 65° C.

100 $\mu l$ 5 M KAc (prepared according to Sambrook et al.) is added and the mixture is incubated for 10 min on ice.

After centrifugation for 10 min at 15000 g, 900 $\mu l$ supernatant is transferred to a new tube containing 550 $\mu l$ isopropanol, and DNA is precipitated by incubation for 15 mm on ice.

DNA is harvested by centrifugation for 10 min at 15000 g, and resolubilised in 200 $\mu l$ TE (10 mM Tris.HCl pH 8.0, 1 mM EDTA).

The solution is extracted once with 200 $\mu l$ phenol/chloroform (1:1) equilibrated with TE and precipitated by addition of 20 $\mu l$ 3M NaAc pH 4.8 and 500 $\mu l$ ethanol.

The DNA is harvested by centrifugation for 10 min at 15000 g, washed with 70% ethanol and dried.

Finally the DNA is resolubilised in 50 $\mu l$ TE.

Southern Blot ca. 5 $\mu g$ of each DNA preparation is digested with EcoRI in a total volume of 100 $\mu l$ for 4 hours. The DNA is precipitated and dissolved in 20 $\mu l$ TE.

The digested samples are run on a 1 % agarose gel with 1×TBE as running buffer.

As molecular weight markers, $^{35}S$ DNA a commercial molecular weight marker (22 Kb–0.06 Kb from Amersham) is used.

After the gel is run, the DNA is depurinated, denatured and transferred to a HYBOND-N hydridisation membrane (Amersham) according to the instructions by the manufacturer. After the transfer, the DNA is fixed by UV crosslinking.

The hybridisation probe is prepared by digestion of pPR70 with NcoI and purification of a fragment of ca. 2000 bp.

The purified fragment is labeled using READY-TO-GO labeling kit (Pharmacia) using deoxycytidine-5'(alpha-$^{32}P$)-triphosphate, triethylammonium sale ~3000 Ci/mmol (Amersham).

The hybridisation is performed according to the instructions of the manufacturer of the hybridisation membranes at high stringency using a washing temperature of 65° C. and following washes 2×SSC, 0.1% SDS, twice, for 15 min, 1×SSC, 0.1% SDS for 15 min and 0.1×SSC, 0.1% SDS for 10 min. The membranes are exposed overnight Transformants giving rise to hybridisations at fragments of 6000 and 1000 bp contain single copy integrated plasmids in the pyrG locus and these transformants are used in the following experiments.

Transformants giving rise to other combinations of hybridisations are discarded.

EXAMPLE 8

Growth Experiment of Single Copy Transformants

The selected transformants are grown in 100 ml of the following medium in 300 ml shake flasks:

| Per liter | 100 ml | Basal salt solution |
| --- | --- | --- |
| | 1 ml | Trace element solution (Vishniak's solution) |

-continued

| | | |
|---|---|---|
| 10 ml | 1M (NH$_4$)$_2$SO$_4$ | |
| 14.7 g | triSodium citrate | |

After autoclaving, 100 ml 20% xylose and 100 ml 2% casein hydrolysate is added, under sterile conditions. 10 ml 100 mM uridine is added to the control flask in view of AB 6-4's uridine requirement, satisfied by the vector in the transformants.

The flasks are inoculated with 10$^5$ spores per ml and incubated in an orbital shaker at 30° C.

After 64 hours the alpha-amylase activities of the supernatants are analyzed, as follows:

Alpha-amylase activities are measured in microtiter plates. 175 ul buffer (50 mM citrate buffer, pH 6.5, 5 mM CaCl$_2$) are mixed with 25 ul sample in each well. The reaction is started by addition of 50 ul CERALPHA substrate (MegaZyme, Canberra, Australia) to the well. The plate is incubated at 37° C. After 15 and 30 minutes 100 ul of the reaction is transferred to a new well containing 150 ul stop buffer (1% trizma base).

The substrate is a chromogenic substrate which is composed of a heptamaltose where nitrophenyl is coupled to the reducing end, and the nonreducing end is blocked by another group. Upon digestion of an internal α1,4 bond α-glucosidases which are included into the substrate degrade the now unblocked substrate and release the yellow compound p-nitrophenol.

The activity is measured in an Elisa reader at wavelength 405 nm. The activity calculated as the rise in absorbance in 15 min.

The following results are obtained:

TABLE 2

| | α-amylase activity | | |
|---|---|---|---|
| | experiment 1 | experiment 2 | average |
| *Aspergillus niger* AB6-4 | 0.137 | 0.097 | 0.117 |
| AB6A::pPR70 | 2.816 | 2.909 | 2.863 |
| AB64::pPR70-6 | 0.440 | 0.273 | 0.356 |
| AB64::pPR70-16 | 2.725 | 2.907 | 2.816 |
| AB64::pPR70-3 | 1.005 | 0.749 | 0.877 |
| AB64::pPR70-5 | 0.872 | — | 0.872 |
| AB6A::pPR70-4 | 0.307 | 0.159 | 0.233 |

These results show that there is a optimal number of xlnB elements of three. Deletion of one element gives a 6 fold reduction in activity. When more elements are added the activity drops more progressively.

EXAMPLE 9

Growth of *Aspergillus niger* AB6-4 Transformants with pPR70 and pPR70-6

The untransformed host *A. niger* AB6-4 and transformants with a single copy of pPR70 and pPR70-6 integrated therein, as determined in example 8, are grown in 100 ml of the following medium in 300 ml shake flasks:

| Per liter | 100 ml | Basal salt solution |
|---|---|---|
| | 1 ml | Trace element solution (Vishniak's solution) |

-continued

| | | |
|---|---|---|
| 10 ml | 1M (NH$_4$)$_2$SO$_4$ | |
| 14.7 g | triSodium citrate | |

After autoclaving, 100 ml 20% xylose and 100 ml 2% casein hydrolysate is added under sterile conditions. 10mM uridine is added to the flask containing the untransformed host.

The flasks are inoculated with 10$^5$ spores per ml and incubated in an orbital shaker at 30° C. After 64 hours α-amylase activities of the supernatants are analysed according to example 6 and high α-amylose activity is found in the flask with the transformed fungus whereas no activity is found in the flask containing the untransformed host.

For visualisation of the results, 5 and 20 μl of the culture broth is loaded on a precast 12% Tris-Glycine gel (NOVEX, San Diego, Calif.) according to the instructions supplied by the manufacturer. As a molecular weight marker, a commercially available low molecular weight marker 14.4-94 KD (Pharmacia) is used.

Figure 9:
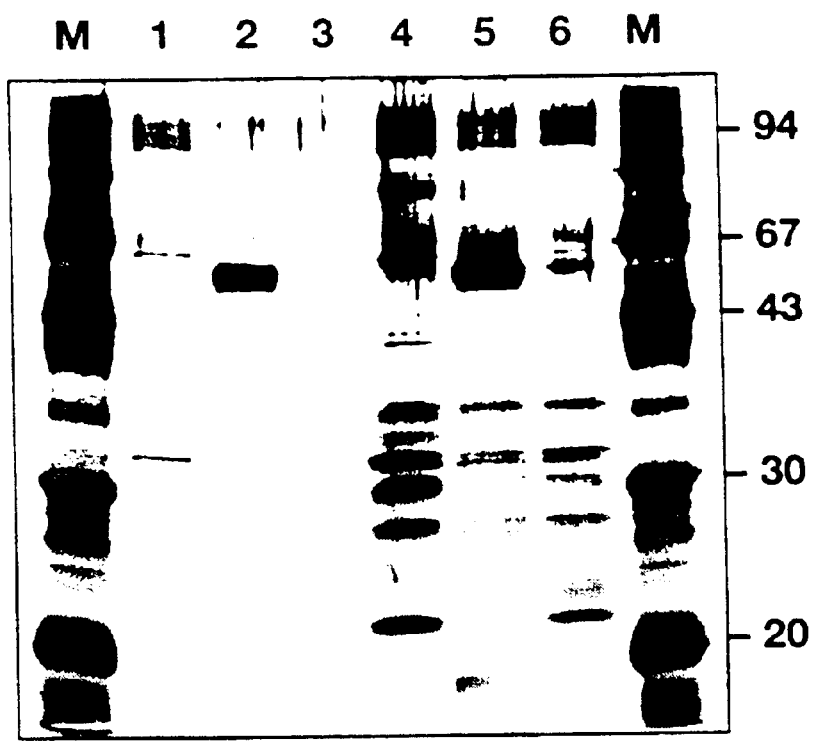
FIG. 9 shows a silver-stained gel of the products derived from *A. niger* transformed with pPR70 and pPR70-6.

The gel is silver stained. In the untransformed host only very weak bands are visible. In the transformant in addition to the weak bands seen in the untransformed host a strong band appears at 54 KD which corresponds the mobility of Thermomyces lanuginosus α-amylase. The strength of this band is reduced, almost to invisibility, in pPR70-6 (See FIG. 9).

Silver staining procedure:

After electrophoresis the gel is soaked in 50% Ethanol, 12% acetic acid, 0.05% of 37% formaldehyde for one hour or more to fix the proteins.

The gel is washed in 50% ethanol three times for 20 min.

Soaked 1 min in 0.2 g/l Na$_2$SO$_3$.5H2O.

Washed 3 times for 20 seconds in water.

Soaked in 2 g/l AgNO$_3$, 750 μl of 37% formaldehyde for 20 min.

Washed two times for 20 seconds in water.

Colour is developed in (per liter: 60 g Na$_2$CO$_3$, 500 μl of 37% formaldehyde, 20 ml of 0.2 g/l Na$_2$S$_2$O$_3$-5H$_2$O) until the bands appears clear.

The gel is washed two times for 2 min in water

The reaction is stopped by soaking the gel in 50% ethanol, 12% acetic acid for 10 min.

The gel is washed for 20 min or longer in 50% ethanol

Soaked in 3% glycerol, 1% acetic acid for 2 hours or longer. The gel is then photographed or dried in a gel dryer for longer storage.

EXAMPLE 10

Expression of Xylanase A Under the Control of the xlnB Promoter

A 400 bp PCR fragment containing the xylanase B promoter is inserted in front of the xylanase A structural gene and terminator. The construct is used to transform *A. tubingensis* strain 6M 179, which overproduces xylanase. The hygromycin gene is used as the selection marker in a cotransformation experiment, as in example 2. A total of 232 transformants are screened by a plate assay using 0.25% congo red. Transformants having a large halo diameter are grown in small scale liquid cultures and the xylanase activity in the culture filtrate is measured. The best transformant (T112-1-27) showed a 1.8× increase in xylanase level compared to the untransformed 6M 179 after a 48 hours induction.

Growth/induction Experiments to Obtain High Level of Xylanase A Expression

Figure 10:
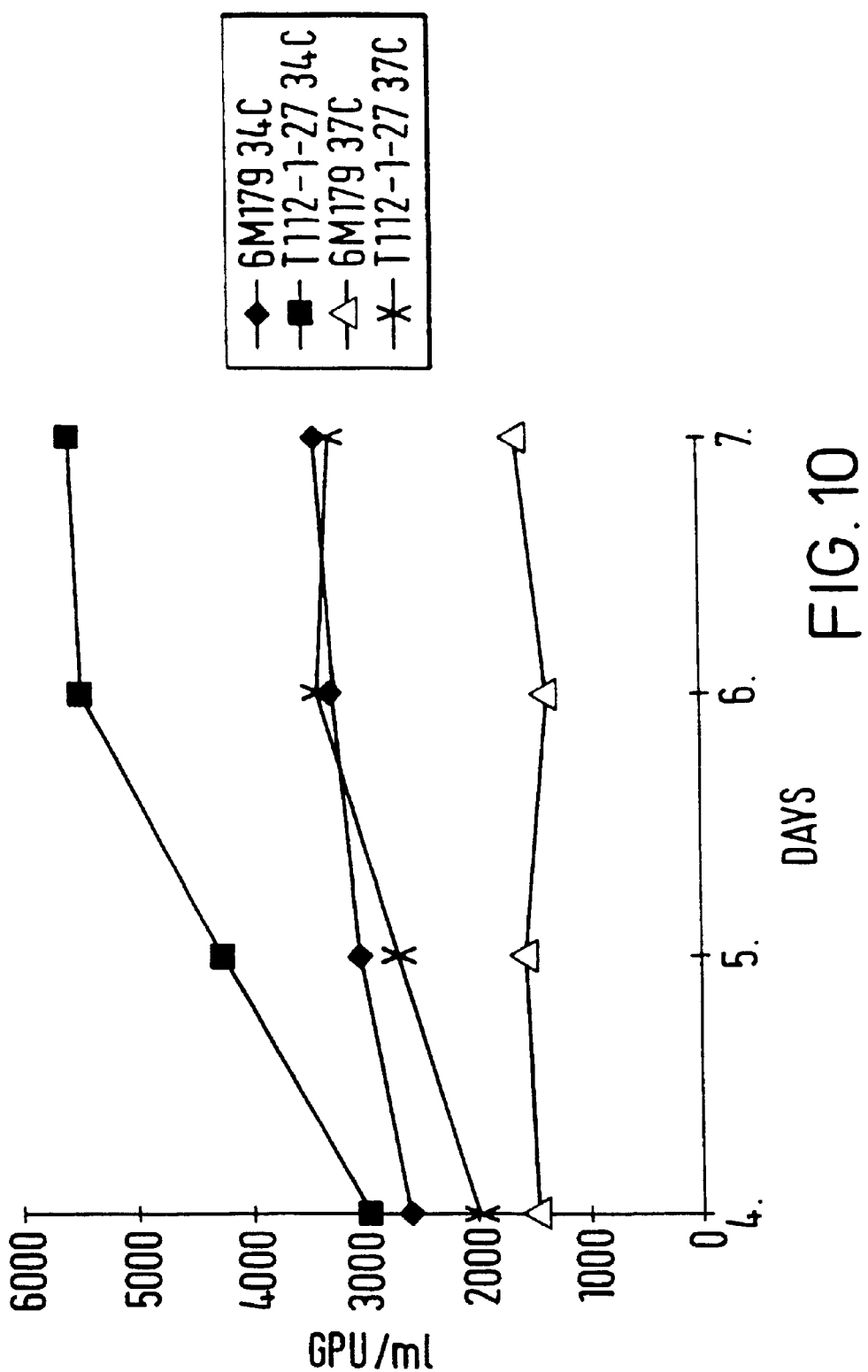
FIG. 10 shows a plot of the results of the cultivation of *A. tubingensis* transformed with a xlnB-xlnA expression construct.

The best transformant (T112-1-27) is grown in large scale fermentation as follows: Spores from the transformant and the control 6M 179 are grown for 7 days in 1 liter of medium containing 25 g FIBREX 610 (fiber), 25 g wheat bran and 1.4 grams of ammonium sulphate. The cultures are grown in duplicate at two different temperatures (34° C. and 37° C.) at 200 rpm and an initial pH of 3.57. Samples of the culture filtrate are collected at days 4, 5, 6 and 7. The samples from day 6 are subjected to anion exchange chromatography using MONO Q anion exchange column and a distinct xylanase A peak is observed. The chromatograph shows a 30% increase in the xylanase A peak for the transformant containing the xylanase B promoter—xylanase A construct when compared to 6M179. The samples are analyzed for xylanase activity expressed as GPU/ml and the results are summarized in Table 3 below and FIG. 10. The results demonstrate increased xylanase A production of around 40%.

TABLE 3

| Cultures | Temperature | GPU/ml day 4 | GPU/ml day 5 | GPU/ml day 6 | GPU/ml day 7 |
| --- | --- | --- | --- | --- | --- |
| 6M179 | 34° C. | 2603 | 3028 | 3261 | 3385 |
| T112-1-27 | 34° C. | 2966 | 4244 | 5445 | 5547 |
| 6M179 | 37° C. | 1475 | 1560 | 1360 | 1626 |
| T112-1-27 | 37° C. | 1984 | 2698 | 3385 | 3289 |

What is claimed is:

1. A method for modulating transcription of a nucleotide sequence, which comprises operatively linking the nucleotide sequence to a xylanase promotor, which xylanase promoter is operatively linked to one or more added nucleic acid elements having the sequence CGGCAGGGTCTC (SEQ ID NO: 7), wherein the total number of nucleic acid elements having the sequence CGGCAGGGTCTC is at least three.

2. The method according to claim 1, wherein the total number of nucleic acid elements having the sequence CGGCAGGGTCTC (SEQ ID NO: 7) to upregulate transcripton of the nucleotide sequence is three.

3. The method according to claim 1, wherein the nucleic acid elements are in an upstream region of the promoter.

4. The method according to claim 1, wherein the nucleotide sequence is a heterologous nucleotide sequence.

5. A method according to claim 1, wherein said xylanase promoter is a xylanase B promoter.

6. A nucleic acid construct comprising a xylanase promoter, which is operatively linked to a nucleotide sequence, and which xylanase promoter comprises at least three copies of a nucleic acid element having the sequence CGGCAGGGTCTC (SEQ ID NO: 7).

7. A method for modulating transcription of a nucleotide sequence, which comprises operatively linking the nucleotide sequence to a xylanase promoter, which xylanase promoter is operatively linked to at least three nucleic acid elements having the sequence CGGCAGGGTCTC (SEQ ID NO: 7).

8. A construct according to claim 6, which contains 3 copies of the nucleic acid element having the sequence CGGCAGGGTCTC (SEQ ID NO: 7).

9. A construct according to claim 6, which comprises 4 or more copies of the nucleic acid element having the sequence CGGCAGGGTCTC (SEQ ID NO: 7).

10. The nucleic acid construct according to claim 6, wherein the nucleic acid element is in an upstream region of the promoter.

11. The nucleic acid construct according to claim 6, wherein the promoter is a fungal promoter.

12. The nucleic acid construct according to claim 6, wherein the nucleotide sequence is a heterologous nucleotide sequence.

13. A nucleic acid construct according to claim 6, wherein said xylanase promoter is a xylanase B promoter.

14. A host cell transformed with a construct according to claim 6.

15. A host cell according to claim 14 which is a plant cell or a fungal cell.

* * * * *